(12) United States Patent
Kamath et al.

(10) Patent No.: US 7,085,348 B2
(45) Date of Patent: Aug. 1, 2006

(54) LEAF SEQUENCING METHOD AND SYSTEM

(75) Inventors: Srijit Kamath, Gainesville, FL (US);
Sartaj Sahni, Gainesville, FL (US);
Jantinder Palta, Gainesville, FL (US);
Sanjay Ranka, Gainesville, FL (US);
Jonathan G. Li, Gainesville, FL (US)

(73) Assignee: The University of Florida Research Foundation, Inc., Gainesville, FL (US)

( * ) Notice: Subject to any disclaimer, the term of this patent is extended or adjusted under 35 U.S.C. 154(b) by 395 days.

(21) Appl. No.: 10/736,023

(22) Filed: Dec. 15, 2003

(65) Prior Publication Data

US 2005/0148841 A1 Jul. 7, 2005

(51) Int. Cl.
*A61N 5/10* (2006.01)
(52) U.S. Cl. .................................................... 378/65
(58) Field of Classification Search ................ 378/65
See application file for complete search history.

(56) References Cited

U.S. PATENT DOCUMENTS

| | | | | |
|---|---|---|---|---|
| 6,330,300 B1 * | 12/2001 | Siochi | ...... | 378/65 |
| 6,477,229 B1 * | 11/2002 | Grosser | ...... | 378/65 |
| 6,661,871 B1 * | 12/2003 | Siochi | ...... | 378/65 |
| 6,795,523 B1 * | 9/2004 | Steinberg | ...... | 378/65 |
| 6,853,705 B1 * | 2/2005 | Chang | ...... | 378/65 |

FOREIGN PATENT DOCUMENTS

WO   WO 99/48558 A1 * 9/1999

OTHER PUBLICATIONS

Langer et al., "Improved leaf sequencing reduces segments or monitor units needed to deliver IMRT using multileaf collimators," Med. Phys., 28:2450-2458, 2001.
Que, W., "Comparison of algorithms for multileaf collimator field segmentation," Med. Phys., 26:2390-2396, 1999.
Que et al., "'Tongue-and-groove' effect in intensity modulated radiotherapy with static multileaf collimator fields," Phys. Med. Biol., 49:399-405, 2004.

(Continued)

*Primary Examiner*—Edward J. Glick
*Assistant Examiner*—Thomas R. Artman
(74) *Attorney, Agent, or Firm*—Akerman Senterfitt; Neil R. Jetter

(57) ABSTRACT

A method of delivering radiation treatment using multi-leaf collimation includes the step of providing a radiation fluence map which includes an intensity profile. The fluence map is converted into a preliminary leaf sequence, wherein the preliminary leaf sequence minimizes machine on-time and is generated without leaf movement constraints. The leaf movement constraint is imposed on the preliminary leaf sequence. At least one constraint elimination algorithm is then applied, the algorithm adjusting the preliminary leaf sequence to minimize violations of the constraint while providing the desired fluence map and minimized radiation on-time. The method can be applied to SMLC and DLMC systems, and can include adjustment for the tongue-and-groove effect.

12 Claims, 19 Drawing Sheets

OTHER PUBLICATIONS

Van Santvoort et al., "Dynamic multileaf collimation without 'tongue-and-groove' underdosage effects," Phys. Med. Biol., 41:2091-2105, 1996.

Xia et al., "Multileaf collimator leaf sequencing algorithm for intensity modulated beams with multiple static segments," Med. Phys., 25:1424-1434, 1998.

* cited by examiner

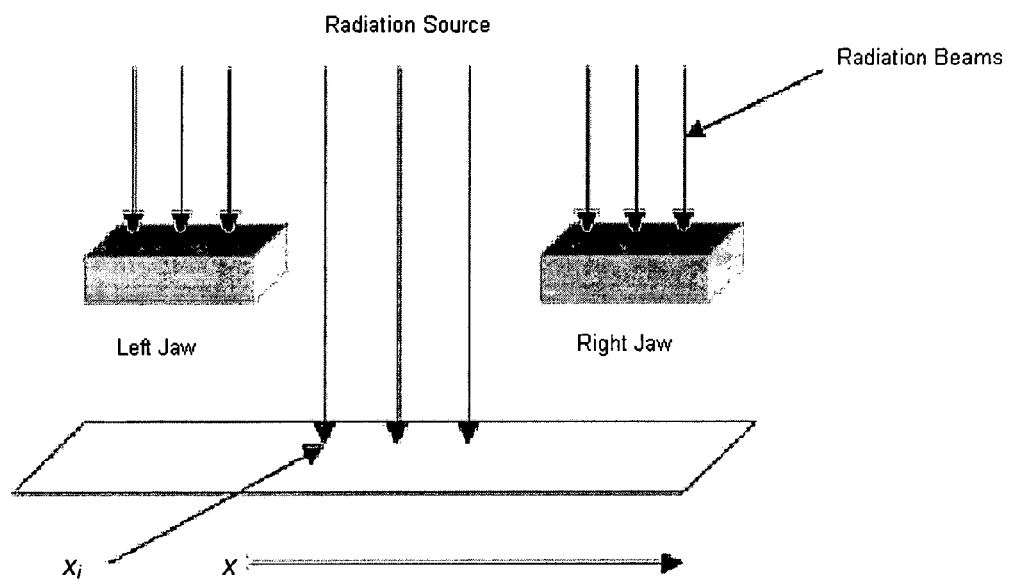
FIG. 4
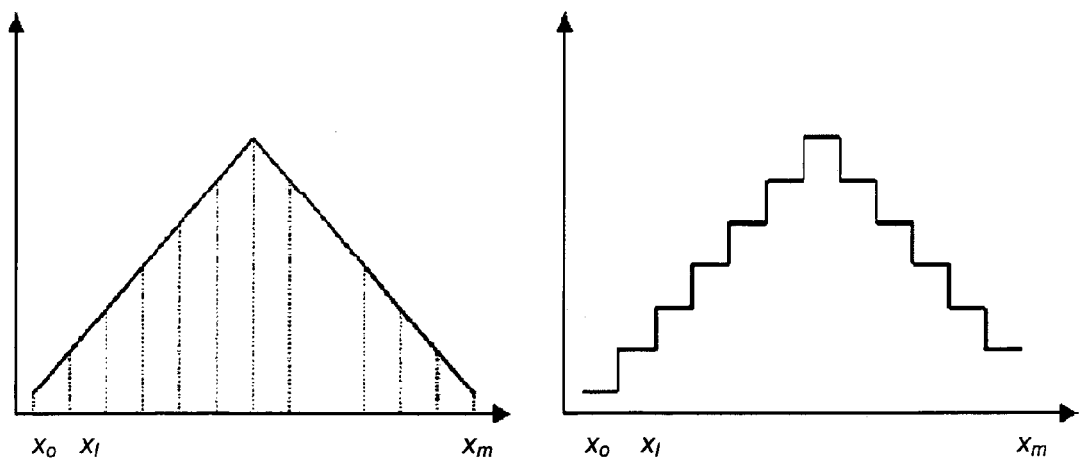
FIG. 5a
FIG. 5b

LEAF SEQUENCING METHOD AND SYSTEM

STATEMENT REGARDING FEDERALLY SPONSORED RESEARCH OR DEVELOPMENT

The United States Government has certain rights to this invention pursuant to NIH Grant/Contract No. LM06659-03.

CROSS-REFERENCE TO RELATED APPLICATIONS

Not applicable.

FIELD OF THE INVENTION

The invention relates to a radiation emitting device, and more particularly, to a system and method for efficiently and more safely delivering radiation treatment to a patient.

BACKGROUND

Radiation emitting devices are generally known and can be used for radiation therapy for the treatment of patients. A radiation therapy device generally includes a gantry which is swiveled around a horizontal axis of rotation in the course of a radiation therapy treatment. A linear accelerator is located in the gantry for generating a high energy radiation beam for the therapy. This high energy radiation beam can be an electron beam or X-ray beam. During treatment, the radiation beam is directed towards a patient lying in the isocenter of the gantry rotation.

To control the radiation emitted toward a given object, a beam shielding device, such as a plate arrangement or a collimator, is typically provided in the trajectory of the radiation beam between the radiation source and the patient. A collimator is a computer-controlled mechanical beam shielding device which generally includes multiple leaves, for example, a plurality of relatively thin plates or rods, typically arranged as opposing leaf pairs. The plates are formed from a relatively dense and radiation impervious material and are generally independently positionable to size and shape of the radiation beam. These leaves move across the tissue being radiated, thus blocking out some areas and filtering others to vary the beam intensity and precisely distribute the radiation dosage.

A multileaf collimator (MLC) is an example of a multileaf beam shielding device that can accurately and efficiently adjust the size and shape of the radiation beam. The size and shape of a radiation beam is designed during the treatment planning process. This is useful for both intensity modulated radiation treatment (IMRT) and three-dimensional conformal radiation therapy (3D CRT).

Traditional radiotherapy utilizes uniform beams of radiation, producing a uniform distribution of dose throughout the irradiated volume, which includes the target volume. This ensures the target is adequately covered, but does nothing to avoid often critical surrounding structures. With IMRT, the beams of radiation are made to be intentionally non-uniform. In this way the dose distribution can be carefully shaped to minimize radiation to surrounding structures.

Measurement unit efficiency is a commonly used measure of beam efficiency. The measurement unit (MU) efficiency is defined as the efficiency with which the incident radiation results dose being in absorbed in the target region of a patient. The consequence of low MU efficiency is an increase in leakage radiation that reaches the surrounding tissue of the patient.

There are several critical components of a successful IMRT program. The first is a process referred to as "inverse planning." Inverse planning utilizes a mathematical algorithm to optimize the intensity of the various beams. This optimization is highly computer intensive.

The second critical process is to convert the intensity distributions obtained, often referred to cumulatively as a fluence map, into a series of MLC leaf movements. This is referred to as "leaf sequencing." Many device-specific factors must be accounted for in this process. These factors include radiation leakage through and between the leaves, leaf speed, dose rate, and the "tongue-and-groove" effect.

IMRT can be performed either while the beam is on, which is referred to as dynamic MLC or DMLC delivery, or by turning the beam off while the leaves move to their next position, which is referred to as segmented MLC or SMLC delivery. The beam shielding device defines a field on the object to which a prescribed amount of radiation is to be delivered. The usual treatment field shape results in a three-dimensional treatment volume which includes segments of normal tissue, thereby limiting the dose that can be given to the target, such as a tumor. The dose delivered to the tumor can be increased and the treatment time decreased as the amount of dose delivered to the normal surrounding tissue is decreased. Although current leaf sequencing algorithms have reduced the radiation level reaching surrounding normal tissue somewhat as compared to traditional uniform beams of radiation, these leaf sequences have not provided optimal MU efficiency.

SUMMARY

A method of delivering radiation treatment using multi-leaf collimation includes the step of (a) providing a radiation fluence map which supplies a desired radiation intensity profile. The fluence map is (b) converted into a preliminary leaf sequence, wherein the preliminary leaf sequence minimizes machine on-time and is generated without any leaf movement constraints. In step (c), a leaf movement constraint is imposed on the preliminary leaf sequence. In the next step (d), at least one constraint elimination algorithm is then applied, the algorithm adjusting the preliminary leaf sequence to minimize violations of the constraint while providing the desired fluence map and minimized radiation on-time. The method can be applied to SMLC and DLMC systems, and can include adjustment for the tongue-and-groove effect.

The leaf movement constraint can comprise a minimum separation distance between adjacent leaves in the leaf pair. In this embodiment, the applying step (d) can comprise (e) modifying at least one leaf pair in the preliminary leaf sequence to form a modified leaf sequence, wherein the modifying step comprises identifying and adjusting positions of leaves in the preliminary leaf sequence which violate the minimum separation distance to provide at least the minimum separation distance, (f) modifying at least one leaf pair in the modified leaf sequence to produce a further modified leaf sequence, the further modified leaf sequence providing the intensity profile, (g) examining the further modified leaf sequence for violations of the minimum separation distance, and (h) iteratively repeating steps (e) and (f) if at least one violation of the minimum separation distance is identified in step (g) using the further modified leaf sequence as the preliminary leaf sequence to generate a corrected leaf sequence. In this embodiment of the invention, the method can further comprise the step of reducing a tongue-and-groove underdose. The step of reducing the tongue-and-groove underdose can comprise applying a tongue-and-groove constraint to the corrected leaf sequence, The step of applying a tongue-and-groove constraint can comprise the steps of (i) modifying at least one leaf pair in the corrected leaf sequence to form a modified corrected leaf sequence, wherein the modifying step comprises identifying and adjusting positions of leaves in the preliminary leaf sequence which violate a tongue-and-groove constraint, (j) modifying at least one leaf pair in the modified corrected leaf sequence to produce a further modified leaf sequence, the further modified leaf sequence providing the fluence map, (k) examining the further modified corrected leaf sequence for violations of tongue-and-groove constraint, and (l) iteratively repeating steps (i) and (j) if at least one violation of the tongue and groove constraint is identified in step (k) using the further modified leaf sequence as the preliminary leaf sequence.

In the embodiment where the multi-leaf collimation is dynamic multi-leaf collimation, the constraint can comprise a leaf interdigitation constraint. In this embodiment, the applying step (d) can comprise (e) modifying at least one leaf pair in the preliminary leaf sequence to form a modified leaf sequence, wherein the modifying step comprises identifying and adjusting positions of leaves in the preliminary leaf sequence which violate the interdigitation constraint, (f) modifying at least one leaf pair in the modified leaf sequence to produce a further modified leaf sequence, the further modified leaf sequence providing the fluence map, (g) examining the further modified leaf sequence for violations of the interdigitation constraint, and (h) iteratively repeating steps (e) and (f) if at least one violation of the interdigitation constraint is identified in step (g) using the further modified leaf sequence as the preliminary leaf sequence.

A method of reducing tongue-and-groove underdose during radiation treatment using multi-leaf collimation can comprise the steps of (a) providing a radiation fluence map, (b) converting the fluence map into a preliminary leaf sequence, wherein the preliminary leaf sequence minimizes a minimum on-time and is generated without any leaf movement constraints, (c) modifying at least one leaf pair in the preliminary leaf sequence to form a modified leaf sequence, wherein the modifying step comprises identifying and adjusting positions of leaves in the preliminary leaf sequence which violate a tongue-and-groove constraint. In the next step (d), at least one leaf pair in the modified leaf sequence is modified to produce a further modified leaf sequence, the further modified leaf sequence providing the desired intensity profile, (e) examining the further modified leaf sequence for violations of the tongue-and-groove constraint, and in step (f) iteratively repeating steps (c) and (d) if at least one violation of the tongue-and-groove constraint is identified in step (e) using the further modified leaf sequence as the preliminary leaf sequence.

A system for delivering radiation treatment using multi-leaf collimation comprises a radiation source for generating a radiation beam, a multi-leaf collimator having a plurality of leafs for shaping the radiation beam, and structure for generating a preliminary leaf sequence from a fluence map which supplies a desired radiation intensity profile, wherein the preliminary leaf sequence minimizes machine on-time and is generated without any leaf movement constraints. The system also includes structure for imposing at least one leaf movement constraint on the preliminary leaf sequence, and structure for applying at least one constraint elimination algorithm for adjusting the preliminary leaf sequence to minimize violations of the constraint while providing the fluence map and minimized on-time. The multi-leaf collimator can be a segmented multi-leaf collimator or a dynamic multi-leaf collimator. The system can include structure for reducing a tongue-and-groove underdose. The constraint can comprise a minimum separation distance between paired leaves. The structure for applying the constraint can comprise structure for modifying at least one leaf pair in the preliminary leaf sequence to form a modified leaf sequence, wherein the structure for modifying comprises structure for identifying and adjusting positions of leaves in the preliminary leaf sequence which violate the minimum separation distance to provide at least the minimum separation distance; structure for modifying at least one leaf pair in the modified leaf sequence to produce a further modified leaf sequence, the further modified leaf sequence providing the desired intensity profile; structure for examining the further modified leaf sequence for violations of the minimum separation distance, and structure for iteratively adjusting the leaf sequence if at least one violation of the minimum separation distance is identified.

BRIEF DESCRIPTION OF THE DRAWINGS

A better understanding of the present invention can be obtained when the following detailed description is considered in conjunction with the following drawings in which:

FIG. 4 shows the geometry and coordinate system used in the Examples provided.

FIG. 5(a) shows a piecewise continuous function while FIG. 5(b) shows the corresponding discretized intensity profile.

FIG. 7(a) shows an intensity profile, while

DETAILED DESCRIPTION OF THE INVENTION

A method of delivering radiation treatment to a patient using multi-leaf collimation includes the steps of providing a radiation fluence map which includes an intensity profile. The fluence map is converted into a preliminary leaf sequence. The preliminary leaf sequence minimizes machine on-time and is generated without leaf movement constraints. The leaf movement constraint is imposed on the preliminary leaf sequence. At least one constraint elimination algorithm is then applied, the algorithm adjusting the preliminary leaf sequence to minimize violations of the constraint while providing the desired fluence map and a minimized radiation on-time.

Figure 1:
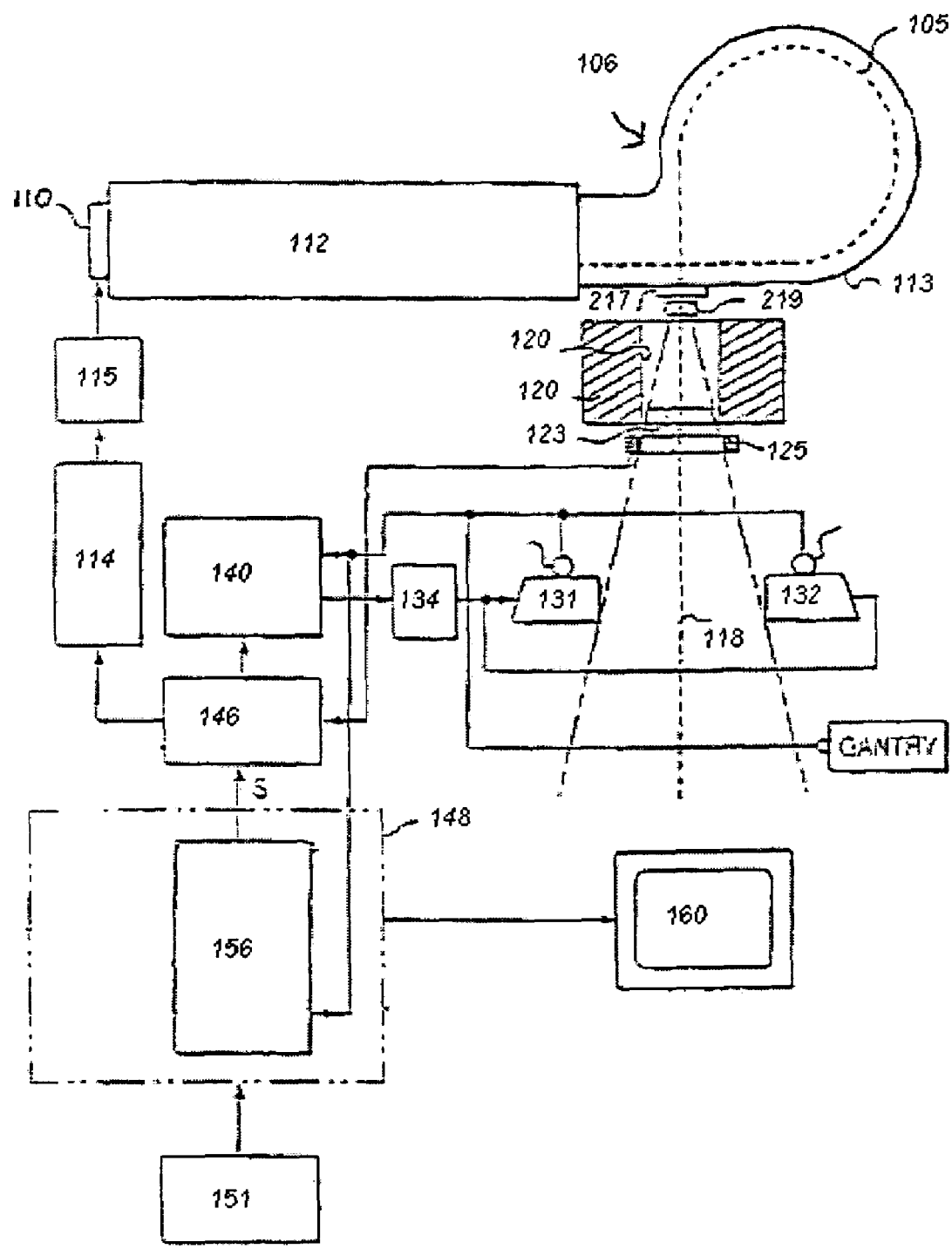
FIG. 1 is a diagram of a radiation treatment device according an embodiment of the invention.

Turning now to FIG. 1, a block diagram of the radiation treatment device 100 according to an embodiment of the invention is shown. An electron beam 105 is generated by an electron accelerator 106. The electron accelerator 106 includes an electron gun 110, a wave guide 112, and an evacuated envelope or guide magnet 113. A triggering system 114 generates injector trigger signals and supplies them to an injector 115. Based on the trigger signals, the injector 115 generates injector pulses which are fed to the electron gun 110 in the accelerator 106 which results in the generation of electron beam 105.

The electron beam 105 is accelerated and guided by wave guide 112. A high frequency signal source (not shown) is also provided, which supplies RF signals for the generation of an electromagnetic field which is supplied to wave guide 112. The electrons injected by the injector 115 and emitted by the electron gun 110 are accelerated by the electromagnetic field in the wave guide 112 and exit at the end opposite to electron gun 110 in electron beam 105. The electron beam 105 then enters guide magnet 113 and from there is guided through window 117 along axis 118. After passing through a first scattering foil 119, the beam goes through an opening 120 of a shield block 122 and encounters a flattening filter 123. Next, the beam is sent through a measuring chamber 125 in which the dose is determined. If the scattering foil 119 is replaced by a target, the radiation beam is an X-ray beam. In this case, the flattening filter 123 may be absent.

Beam shielding device is provided in the path of beam 105, comprising a plurality of opposing plates 131 and 132, only two of which are illustrated for convenience. In one embodiment, other pairs of plates (not shown) are arranged perpendicular to plates 131 and 132. The plates 131 and 132 are moved with respect to axis 118 by a drive unit 134 to change the size and shape of the irradiated field. The drive unit 134 includes an electric motor which is coupled to the plates 131 and 132 and which is controlled by a motor controller 140. Position sensors 144 and 145 are also coupled to the plates 131 and 132, respectively for sensing their positions. As noted above, the plate arrangement may alternatively include a multi-leaf collimator having a plurality of radiation blocking leaves.

The motor controller 140 is coupled to a dosing unit 146 which includes a dosimetry controller and which is coupled to a central processing unit 148 for providing set values for the radiation beam for achieving given isodose curves. The output of the radiation beam is measured by a measuring chamber 125. In response to the deviation between the set values and the actual values, the dose control unit 146 supplies signals to a trigger system 114 which changes in a known manner the pulse repetition frequency so that the deviation between the set values and the actual values of the radiation beam output is minimized. In such a radiation device, the dose delivered is dependent upon movement of the collimator leaves 131 and 132.

The central processing unit 148 is typically programmed by the therapist according to the instructions of an oncologist which performs beam optimization according to the present invention so that the radiation treatment device carries out the prescribed radiation treatment while generally maximizing MU efficiency. The delivery of the radiation treatment is generally input through a keyboard 151, or other suitable data entry device. The central processing unit 148 is further coupled to a dose control unit 146 that generates the desired values of radiation for controlling trigger system 114. The trigger system 114 then adapts the pulse radiation frequency and other parameters in a corresponding, conventional manner. The central processing unit 148 further includes a control unit 156 which controls execution of the software and the opening and closing of the collimator plates 131 and 132 according to the present invention to deliver radiation according to a desired intensity profile generally having optimal MU efficiency. A monitor 160 is also provided.

Figure 2:
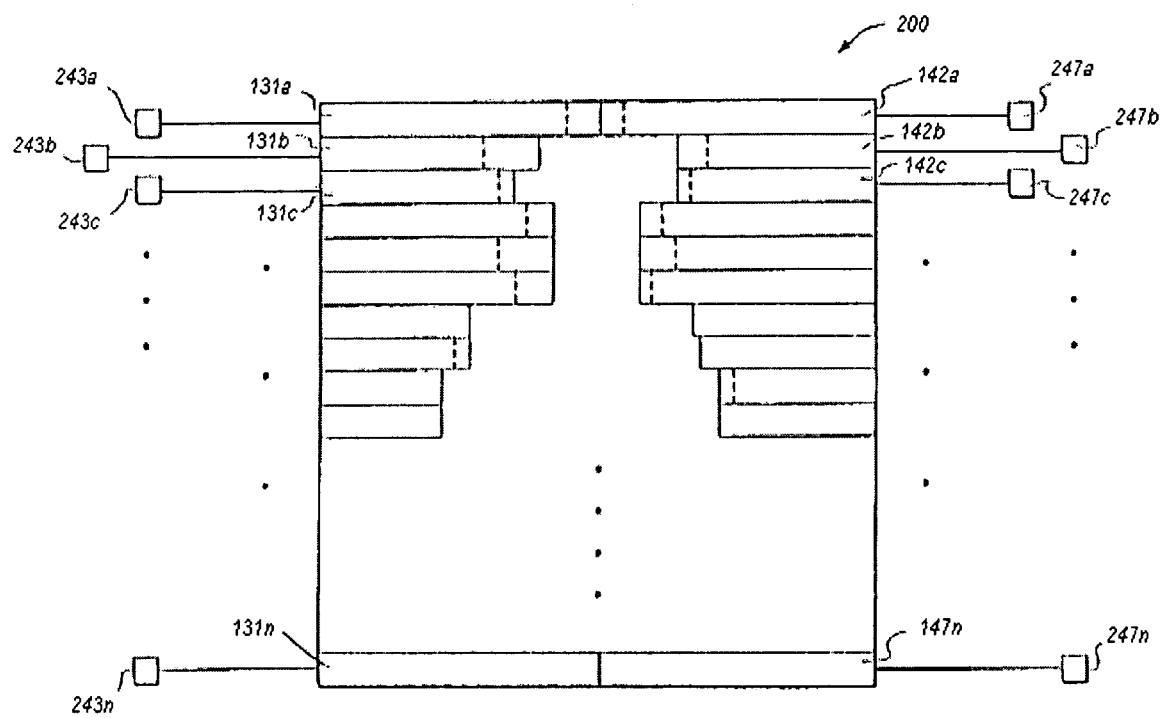
FIG. 2 is a diagram of a multi-leaf collimator according to an embodiment of the invention.

FIG. 2 is a diagram of a multi-leaf collimator 200 according to an embodiment of the invention. Opposing leaf pairs 131a–n, 142a–n, each include a motor or drive unit 243a–n, and 247a–n, respectively. The drive units are controlled by a control unit, such as control unit 156 shown in FIG. 1 which controls execution of the software and the opening and closing of the collimator plates 131a–n and 142a–n according to the present invention to deliver radiation according to a desired intensity profile generally having optimal MU efficiency.

Figure 3:
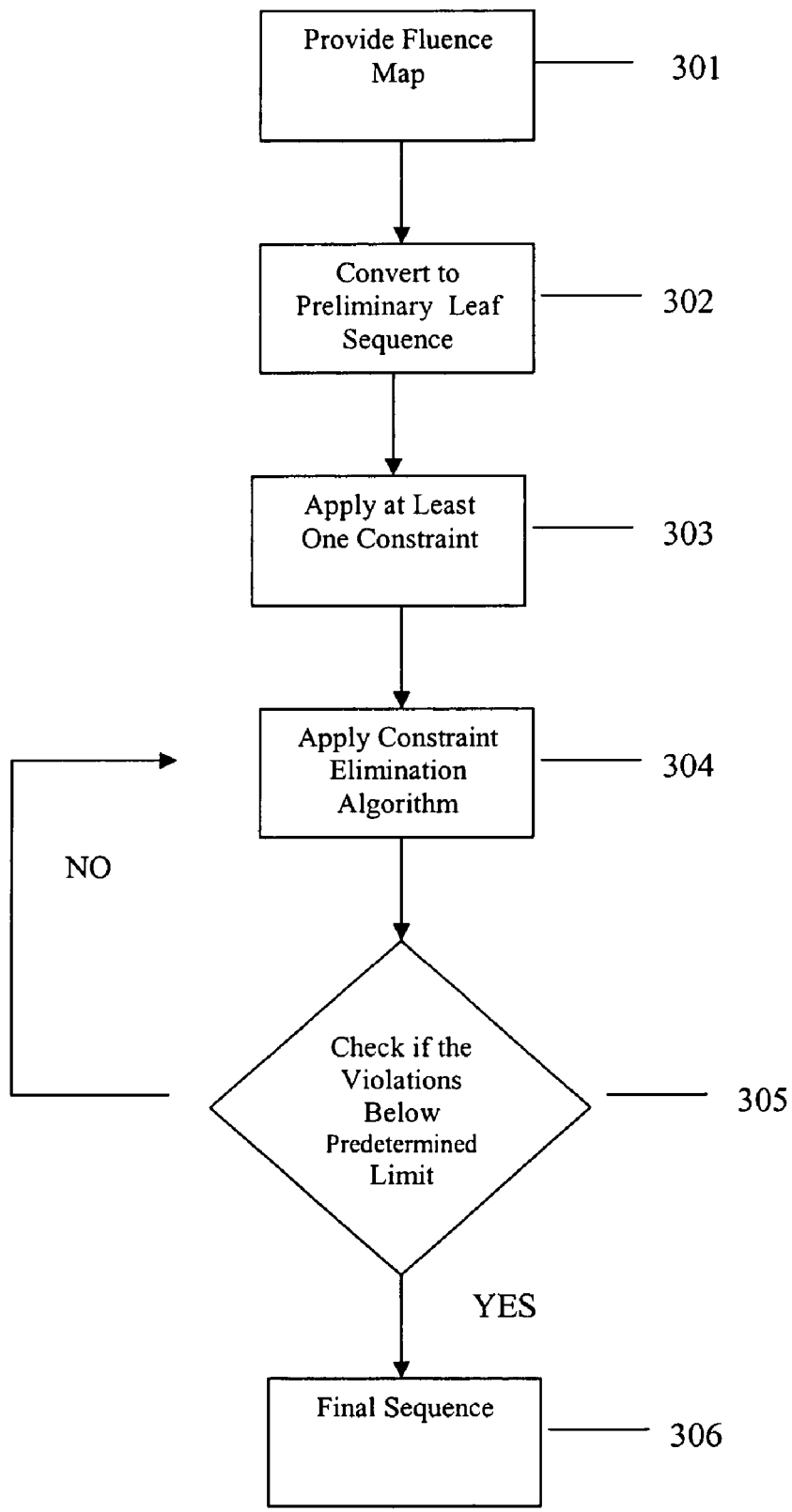
FIG. 3 is a flowchart illustrating a method according to an embodiment of the invention.

FIG. 3 is a flowchart illustrating a method 300 according to an embodiment of the invention. A radiation fluence map is first provided in step 301. In step 302 the fluence map is converted into a preliminary leaf sequence. The preliminary leaf sequence minimizes machine on-time and is generated without any leaf movement constraints. In step 303 at least one leaf movement constraint is imposed on the preliminary leaf sequence. In the case of a segmented multileaf system (SLMC), the constraint includes a minimum leaf separation constraint, while in the case of a dynamic multileaf collimator system (DMLC), the constraint includes an interdigitation constraint.

A tongue and groove constraint may also be applied to the preliminary leaf sequence, or the MU optimized sequence provided by method 300 without initially applying the tongue and groove constraint. A constraint elimination algorithm is then applied in step 304. This algorithm adjusts the preliminary leaf sequence to minimize violations of the constraint identified by the algorithm then further adjusts the leaf sequence to correct for errors induced in the intensity profile by corrections for the imposed constraint. In step 305 the algorithm checks whether the resulting leaf sequence provide violations below a predetermined limit, which can be no violations at all. If the resulting leaf sequence provides violations below a predetermined limit, the method is complete and a final leaf sequence is generated in step 306. If the resulting leaf sequence does not provides violations below a predetermined limit, step 304 is reapplied and the results rechecked in step 305, and so on iteratively, until no violations result. The resulting sequence provides the desired fluence map and minimizes radiation on-time.

In the case of a segmented multileaf system, an algorithm such as the SMLC MINSEPARATION algorithm described in the Examples operates by first solving the problem without any constraint to provide a preliminary leaf sequence that delivers the required intensity of radiation. This can be done using an algorithm such as the algorithm MULTIPAIR described in the Examples. This algorithm has been shown to theoretically generate an optimal MU efficiency leaf sequence without any constraint for SMLC systems.

An algorithm then applies at least one leaf constraint. In this case, a minimum leaf pair separation constraint is generally applied. The algorithm MINSEPARATION can be used beginning with the preliminary leaf sequence determined above. It is possible that the preliminary leaf sequence has violations of the minimum separation constraint, since the constraint was not considered when the preliminary leaf sequence was determined. Violations of the minimum separation constraint refer to time(s) in the sequence that opposing adjacent leaves in a given leaf pair are prescribed to be positioned too close together than is allowed.

The minimum spacing depends on the particular model of the multileaf collimator used, and is generally specified by the manufacturer. Some models have a minimum separation constraint with minimum required spacing typically of the order of about 1 cm. Some models do not have a minimum separation constraint.

Next, the positions of leaves in this sequence are scrutinized, such as starting from left to right leaf pairs progressively. When a given position at which the minimum separation constraint is violated, the constraint elimination algorithm works to eliminate this violation. Corresponding leaf positions in the violating leaf pair(s) are adjusted to insure that the violating leaves are kept at least as far apart as is required to maintain minimum separation, while all other non-violating leaf positions are left unchanged. However, assuming some leaf positions are modified from the original preliminary leaf sequence, the new leaf sequence may no longer deliver the desired intensity profile as dictated by the fluence map provided. Accordingly, further modifications to leaf pairs involved in the violation are generally required to maintain the same intensity profile as before. Once these modifications are applied, one constraint would be eliminated from violation from the original sequence, yet the same intensity profile will be maintained.

Next, further violations of minimum separation in the modified leaf sequence that result from adjustments to recover the intensity profile as described above are identified and corrected. The process of correction for the intensity profile, then the leaf separation constraint, and so on, are iteratively repeated until all violations of the minimum separation constraint are eliminated.

It is possible that at some point in time, an intermediate leaf sequence generated is such that the leaves of a single leaf pair come too close together. In this case no feasible leaf sequence that delivers the exact desired intensity profile while also satisfying the minimum separation constraint may be possible. If this happens, the occurrence of which is preferably checked after every leaf modification to recover the intensity profile, the algorithm is terminated and no leaf sequence is generated. In such cases it is not possible to generate a leaf sequence that delivers the exact desired intensity profile. In this case, the inventive algorithm will not generate a leaf sequence as it will terminate without generating a profile. However, those having ordinary skill in the art will realize that a modified leaf sequencing algorithm can be designed to provide an approximate profile that can be generated in cases where an exact profile is not possible.

If the intermediate leaf sequence generated is such that the leaves of a single leaf pair never come too close together, a leaf sequence is generated in which there are no further violations and which (theoretically) delivers the exact desired intensity. This sequence provides the optimal MU leaf sequence.

The resulting leaf sequence has optimal MU efficiency because whenever a minimum separation constraint violation is detected, it is eliminated. The modifications applied to the leaf sequence to correct the intensity profile are such that they result in minimum loss of MU efficiency as possible for elimination of that particular instance of constraint violation. In other words, any other mechanism for elimination of that violation would result in higher loss of MU efficiency than the modification applied to recover the intensity profile. Since this is generally true every time the algorithm to correct for the intensity profile is applied, the final leaf sequence has minimum loss of MU efficiency, thus providing a maximum MU efficiency or being optimal in MU efficiency.

In the case of a dynamic multileaf system (DMLC), an algorithm, such as DMLC_INTERDIGITATION described in the Examples is applied without leaf constraints. This algorithm is the generally the same as the algorithm MINSEPARATION described for SMLC systems. However, the algorithm DMLC_MULTIPAIR is used which is a version of an algorithm MULTIPAIR applicable to dynamic multileaf collimation (DMLC). The constraint used for DMLC systems is referred to as the interdigitation constraint (see Examples), as opposed to the minimum separation constraint described relative to the SMLC systems. The resulting modifications applied in this case are thus analogous, although different as compared to modifications for SMLC based systems according to the invention.

For DMLC systems, there is no need to check whether a feasible leaf sequence results since the algorithm provided generally always results in a feasible optimal leaf sequence. So leaf sequence adjustments for the interdigitation constraint followed by adjustments to recover the intensity profile are applied iteratively until no violations remain. At this point the algorithm terminates and provides a leaf sequence with optimal MU efficiency.

The invention can also be applied to correct for the tongue-and-groove effect. The tongue-and-groove effect results because in most multileaf collimators, the cross section of the leaves is not entirely rectangular. Rather, there is a tongue and groove overlap arrangement at the interface between adjacent leaves. The regions of the patient's body that fall below the tongue and groove overlap regions typically receive less radiation than is desired because these regions are shielded from the radiation when either of the two adjacent leaves shields the area adjacent to it. In some cases it is possible that some of these regions may not receive any radiation at all though a certain amount of radiation has been prescribed to be delivered at these. To substantially reduce the resulting tongue-and-groove underdose, the invention provides algorithms to sequence the leaves as described below and in the Examples.

The working of Algorithm TONGUEANDGROOVE described in the examples is generally the same as the algorithm MINSEPARATION disclosed herein for SMLC systems according to the invention, except for certain minor differences. In this case, the constraint being considered is the tongue-and-groove constraint, and not the minimum separation constraint as above to form the preliminary leaf sequence. The working of the algorithm TONGUEAND-GROOVE-ID described in the Examples is the same as Algorithm MINSEPARATION except the constraint considered is the tongue-and-groove-id constraint (tongue-and-groove and interdigitation) and not the minimum separation constraint as above. The leaf sequence is then iteratively modified between adjustments for violations of the tongue-and-groove constraint and then violations of the resulting intensity profile analogous to the iterations described above for SMLC and DMLC systems above until no violations remain. A feasible leaf sequence generally always results. The resulting leaf sequence thus provides optimal MU efficiency.

EXAMPLES

It should be understood that the examples and embodiments described herein are for illustrative purposes only and that various modifications or changes in light thereof will be suggested to persons skilled in the art and are to be included within the spirit and purview of this application. The invention can take other specific forms without departing from the spirit or essential attributes thereof.

Example 1

Leaf Sequencing Algorithms for Segmented Multileaf Collimation

The geometry and coordinate system used in this Example (and the other Examples) are shown in FIG. 4. Delivery of profiles that are piecewise continuous are considered. Let $I(x)$ be the desired intensity profile. The profiles first discretized to obtain the values at sample points $x_0, x_1, x_2, \ldots, x_m$. $I(x)$ is assigned the value $I(x_i)$ for $x_i \leq x < x_{i+1}$, for each i. Now, $I(x_i)$ is the desired intensity profile. FIG. 5(a) shows a piecewise continuous function while FIG. 5(b) shows the corresponding discretized profile. The discretized profile can be efficiently delivered with the SMLC method. However, a SMLC sequence can be transformed to a dynamic leaf sequence by allowing both leaves to start at the same point and close together at the same point, so that they sweep across the same spatial interval.

Figure 6:
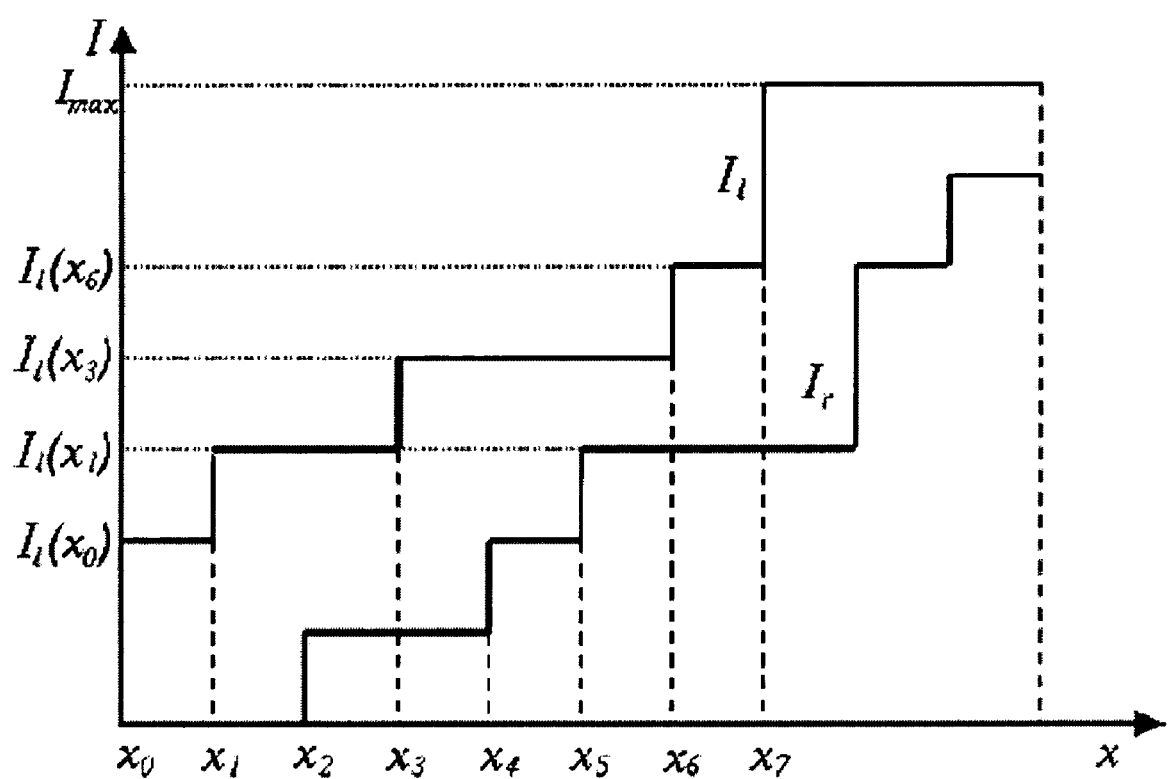
FIG. 6 illustrates an exemplary leaf trajectory during SMLC delivery.

In this analysis it is assumed that the beam delivery begins when the pair of leaves is at the left most position. The initial position of the leaves is at $x_0$. FIG. 6 illustrates the leaf trajectory during SMLC delivery. Let $I_l(x_i)$ and $I_r(x_i)$ respectively denote the amount of Monitor Units (MUs) delivered when the left and right leaves leave position $x_i$. Consider the motion of the left leaf. The left leaf begins at $x_0$ and remains here until $I_l(x_0)$ MUs have been delivered. At this time the left leaf is moved to $x_1$, where it remains until $I_l(x_1)$ MUs have been delivered. The left leaf then moves to $x_3$ where it remains until $I_l(x_3)$ MUs have been delivered. At this time, the left leaf is moved to $x_6$, where it remains until $I_l(x_6)$ MUs have been delivered. The final movement of the left leaf is to $x_7$, where it remains until $I_l(x_7) = I_{max}$ MUs have been delivered. At this time the machine is turned off. The total therapy time, $TT(I_l, I_r)$, is the time needed to deliver $I_{max}$ MUs. The right leaf starts at $x_2$; moves to $x_4$ when $I_r(x_2)$ MUs have been delivered; moves to $x_5$ when $I_r(x_4)$ MUs have been delivered and so on. Note that the machine is off when a leaf is in motion.

The following observations can be made. All MUs that are delivered along a radiation beam along $x_i$ before the left leaf passes $x_i$ fall on it. The greater the x value, the later the leaf passes that position. Therefore $I_l(x_i)$ is a non-decreasing function.

All MUs that are delivered along a radiation beam along $x_i$ before the right leaf passes $x_i$, are blocked by the leaf. The greater the x value, the later the leaf passes that position. Therefore $I_r(x_i)$ is also a non-decreasing function.

From these observations it is noted that the net amount of MUs delivered at a given point is given by $I_l(x_i) - I_r(x_i)$, which must be the same as the desired profile $I(x_i)$.

When the movement of leaves is restricted to only one direction, both the left and right leaves move along the positive x direction, from left to right (FIG. 4). Once the desired intensity profile, $I(x_i)$ is known, one problem becomes that of determining the individual intensity profiles to be delivered by the left and right leaves, $I_l$ and $I_r$ such that:

$$I(x_i) = I_l(x_i) - I_r(x_i), \quad 0 \leq i \leq m \quad (1)$$

Where $(I_l, I_r)$ is referred to as the treatment plan (or simply the plan) for I. Once the plan is obtained, it is possible to determine the movement of both left and right leaves during the therapy. For each i, the left leaf can be allowed to pass $x_i$ when the source has delivered $I_l(x_i)$ MUs. Also, the right leaf can be allowed to pass $x_i$ when the source has delivered $I_r(x_i)$ MUs. In this manner the unidirectional leaf movement profiles for a plan are determined.

Figure 7A:
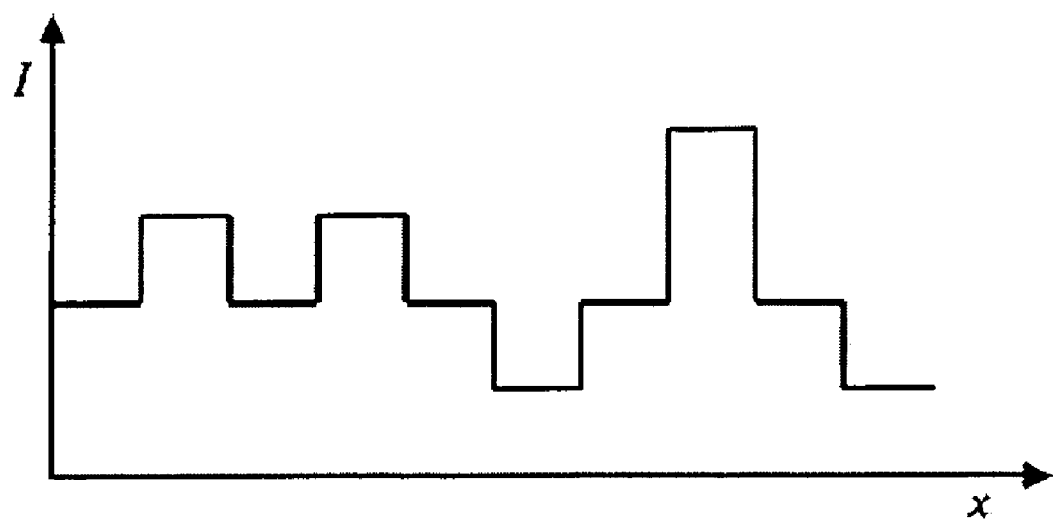
Figure 7B:
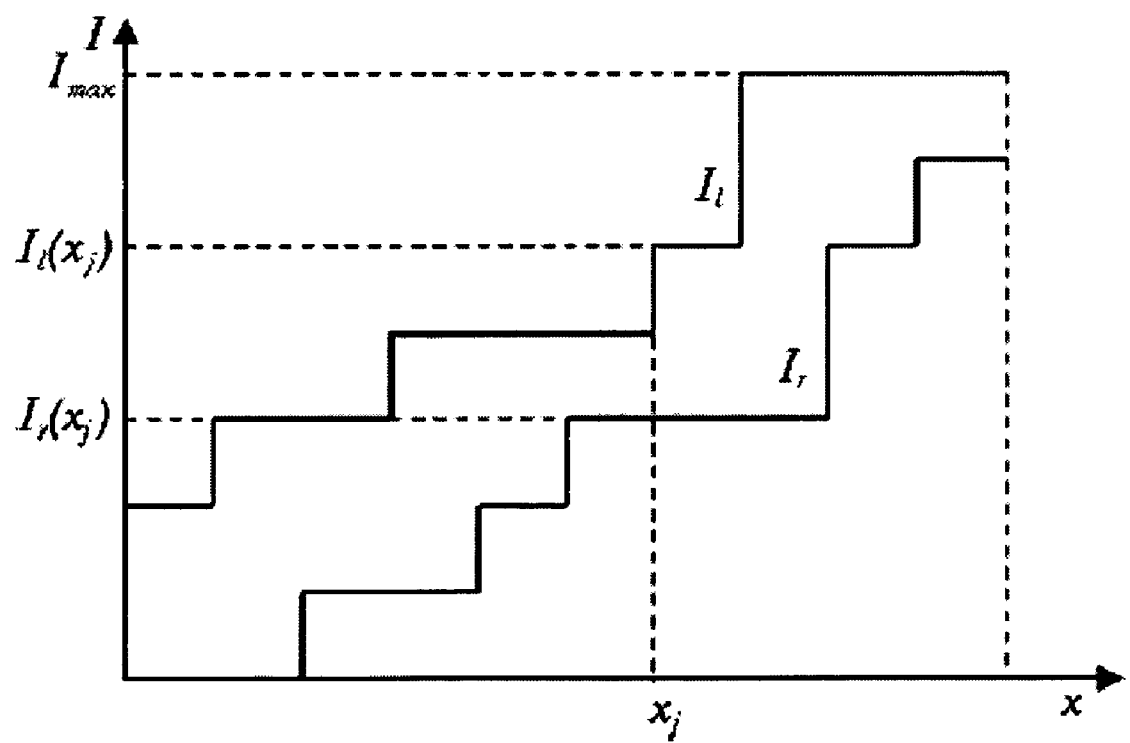
FIG. 7(b) shows the corresponding plan obtained using the algorithm SINGLEPAIR.

From Equation 1, one way to determine $I_l$ and $I_r$ from the given target profile I is to begin with $I_l(x_0) = I(x_0)$ and $I_r(x_0) = 0$; examine the remaining $x_i$s from left to right; increase $I_l$ whenever I increases; and increase $I_r$ whenever I decreases. Once $I_l$ and $I_r$ are determined the leaf movement profiles are obtained as explained in the previous section. The resulting algorithm SINGLEPAIR is shown below. FIG. 7(a) shows the intensity profile while FIG. 7(b) shows the corresponding plan obtained using this algorithm.

Algorithm SINGLEPAIR
$I_l(x_0) = I(x_0)$
$I_r(x_0) = 0$
For j=1 to m do
  If $(I(x_j) \geq I(x_{j-1}))$
    $I_l(x_j) = I_l(x_{j-1}) + I(x_j) - I(x_{j-1})$
    $I_r(x_j) = I_r(x_{j-1})$
  Else
    $I_r(x_j) = I_r(x_{j-1}) + I(x_j) - I(x_{j-1})$
    $I_l(x_j) = I_l(x_{j-1})$
End for Theorem 1. It can be shown that the algorithm SINGLEPAIR obtains plans that are optimal in therapy time.

Corollary 1. Let $I(x_i)$, $0 \leq i \leq m$ be a desired profile. Let $I_l(x_i)$, and $I_r(x_i)$, $0 \leq i \leq m$ be the left and right leaf profiles generated by Algorithm SINGLEPAIR. $I_l(x_i)$ and $I_r(x_i)$, $0 \leq i \leq m$ can be shown to define optimal therapy time unidirectional left and right leaf profiles for $I(x_i)$, $0 \leq i \leq m$. The optimal therapy profiles proof follows from Theorem 1.

In the remainder of this example, $(I_l, I_r)$ is the optimal treatment plan for the desired profile I.

The following observations are made about the optimal treatment plan $(I_l, I_r)$ generated using Algorithm SINGLEPAIR.

Lemma 1. At each $x_i$ at most one of the profiles $I_l$ and $I_r$ changes (increases).

Lemma 2. Let $(I_L, I_R)$ be any treatment plan for I.
(a) $\Delta(x_i) = I_L(x_i) - I_l(x_i) = I_R(x_i) - I_r(x_i) \geq 0$, $0 \leq i \leq m$.
(b) $\Delta(x_i)$ is a non-decreasing function.

Theorem 2. If the optimal plan $(I_l, I_r)$ violates the minimum separation constraint, then there is no plan for I that does not violate the minimum separation constraint.

The separation between the leaves is determined by the difference in x values of the leaves when the source has delivered a certain amount of MUs. The minimum separation of the leaves is the minimum separation between the two profiles. This is referred to as the minimum separation $S_{ud-min}$. When the optimal plan obtained using Algorithm SINGLEPAIR is delivered, the minimum separation is $S_{ud-min(opt)}$.

Corollary 2. Let $S_{ud-min(opt)}$ be the minimum leaf separation in the plan $(I_l, I_r)$. Let $S_{ud-min}$ be the minimum leaf separation in any (not necessarily optimal) given unidirectional plan. $S_{ud-min} \leq S_{ud-min(opt)}$.

Beam delivery when bi-directional movement of leaves is permitted is now examined. Whether relaxing the unidirectional movement constraint helps improve the efficiency of treatment plan is considered.

For a given leaf (left or right) movement profile any x-coordinate can be classified as follows. Draw a vertical line at x. If the line cuts the leaf profile exactly once x is called an unidirectional point of that leaf profile. If the line cuts the profile more than once, x is a bi-directional point of that profile. A leaf movement profile that has at least one bi-directional point is a bi-directional profile. All profiles that are not bi-directional are unidirectional profiles. Any profile can be partitioned into segments such that each segment is a unidirectional profile. When the number of such partitions is minimal, each partition is called a stage of the original profile. Thus unidirectional profiles consist of exactly one stage while bi-directional profiles always have more than one stage.

Figure 8:
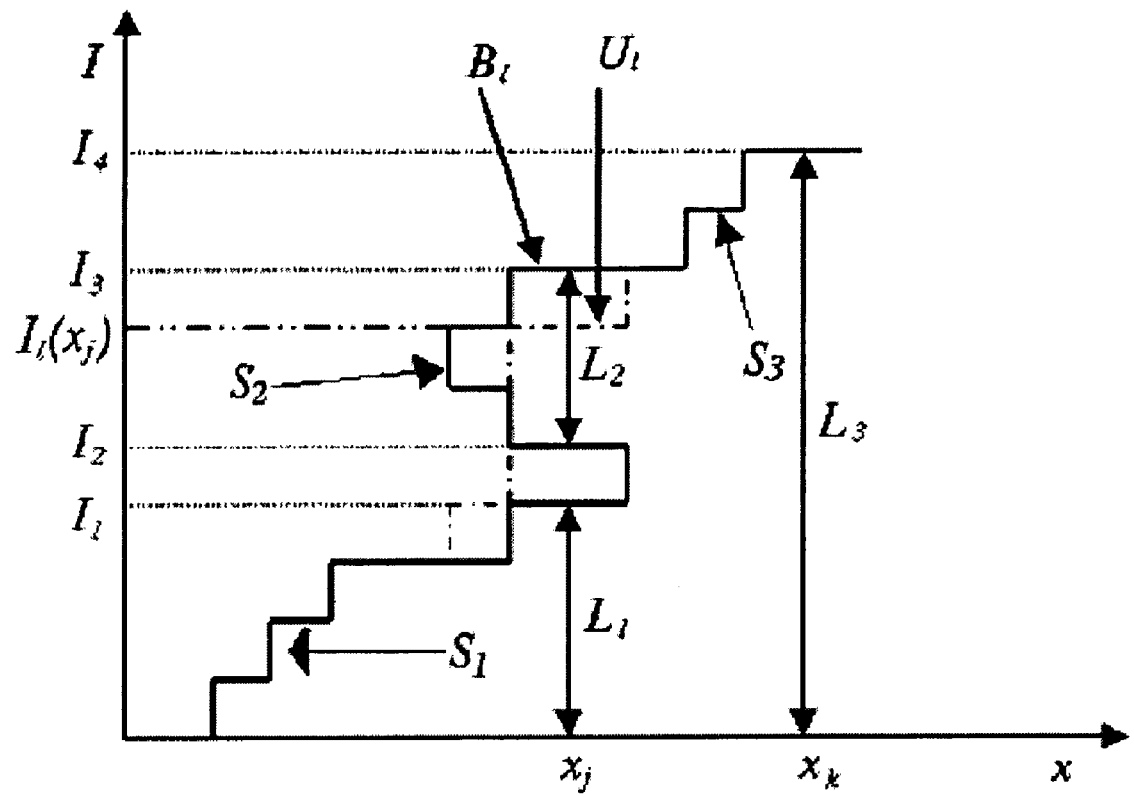
FIG. 8 shows is leaf movement profile demonstrating bi-directional movement.

Now referring to FIG. 8, the leaf movement profile, $B_l$, shows the position of the left leaf as a function of the amount of MUs delivered by the source. The leaf starts from the left edge and moves in both directions during the therapy. Clearly, $B_l$ is bi-directional. The movement profile of this leaf consists of stages $S_1, S_2$ and $S_3$. In stages $S_1$ and $S_3$ the leaf moves from left to right while in stage $S_2$ the leaf moves from right to left. $x_j$ is a bi-directional point of $B_l$. The amount of MUs delivered at $x_j$ is $L_1 + L_2$. In stage $S_1$, when $L_1$ amount of MUs have been delivered, the leaf passes $x_j$. Now, no MU is delivered at $x_j$ till the leaf passes over $x_j$ in $S_2$. Further, $L_2$ MUs are delivered to $x_j$ in stages $S_2$ and $S_3$. Thus, $I_l(x_j) = L_1 + L_2$. Here, $L_1 = I_1$, $L_2 = I_3 - I_2$. $x_k$ is a unidirectional point of $B_l$. The MUs delivered at $x_k$ are $L_3 = I_4$. Note that the intensity profile $I_l$ is different from the leaf movement profile $B_l$, unlike in the unidirectional case.

Lemma 3. Let $(I_l, I_r)$ be a plan delivered by the bidirectional leaf movement profile pair $(B_l, B_r)$ (i.e., $B_l$ and $B_r$ are, respectively, the left and right leaf movement profiles)
(a) $I_l$ is non-decreasing.
(b) $I_r$ is non-decreasing.

From Lemma 3 it is noted that a bidirectional leaf movement profile B delivers a non-decreasing intensity profile. This non-decreasing intensity profile can also be delivered using a unidirectional leaf movement profile as described earlier. This profile is referred to as the unidirectional leaf movement profile that corresponds to the bidirectional profile B and will be denoted by U to emphasize that it is unidirectional. Thus, every bi-directional leaf movement profile has a corresponding unidirectional leaf profile that delivers the same amount of MUs at each $x_i$ as does the bi-directional profile.

Theorem 3. The unidirectional treatment plan constructed by Algorithm SINGLEPAIR is optimal in therapy time even when bidirectional leaf movement is permitted.

Let $U_l$ and $U_r$ be unidirectional leaf movement profiles that deliver the desired profile $I(x_i)$. Let $B_l$ and $B_r$ be a set of bi-directional left and right leaf profiles such that $U_l$ and $U_r$ correspond to $B_l$ and $B_r$ respectively, i.e., $(B_l, B_r)$ delivers the same plan as $(U_l, U_r)$. The minimum separation of leaves in this bidirectional plan is referred to herein as $(B_l, B_r) S_{bd-min}$.

Theorem 4. $S_{bd-min} \leq S_{ud-min}$ for a bi-directional leaf movement profile pair and its corresponding unidirectional profile.

Theorem 5. If the optimal unidirectional plan $(I_l, I_r)$ violates the minimum separation constraint, then there is no bi-directional movement plan that does not violate the minimum separation constraint.

Figure 9:
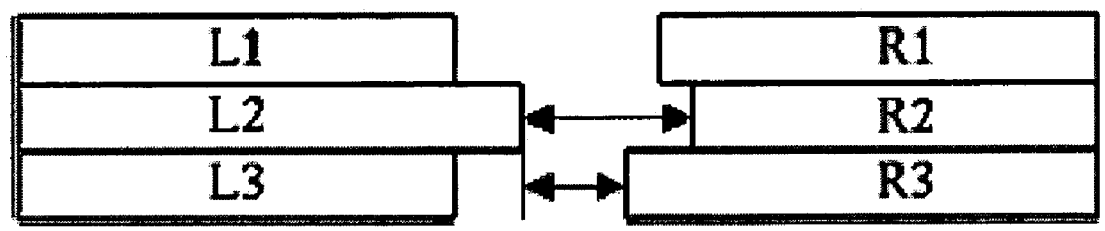
FIG. 9 shows an MLC having three pairs of leaves.

In this example portion, a single pair of leaves is used to deliver intensity profiles defined along the axis of the pair of leaves. However, in a real application, it is required to deliver intensity profiles defined over a 2-D region. Multi-Leaf Collimators (MLCs) are used to deliver such profiles. An MLC is composed of multiple pairs of leaves with parallel axes. FIG. 9 shows an MLC that includes three pairs of leaves—(L1,R1), (L2,R2) and (L3,R3). L1,L2,L3 are left leaves and R1,R2,R3 are right leaves. Each pair of leaves is controlled independently. If there are no constraints on the leaf movements, the desired profile is divided into a set of parallel profiles defined along the axes of the leaf pairs. Each leaf pair i then delivers the plan for the corresponding intensity profile $I_i(x)$. The set of plans of all leaf pairs forms the solution set. This set is referred to as the treatment schedule (or simply, the schedule).

In practical situations, however, there are some constraints on the movement of the leaves. As shown above, the minimum separation constraint requires that opposing pairs of leaves be separated by at least some distance ($S_{min}$) at all times during beam delivery. In MLCs this constraint is applied not only to opposing pairs of leaves, but also to opposing leaves of neighboring pairs. For example, in FIG. 9, L1 and R1, L2 and R2, L3 and R3, L1 and R2, L2 and R1, L2 and R3, L3 and R2 are pairwise subject to the constraint. The term intra-pair minimum separation constraint is used to refer to the constraint imposed on an opposing pair of leaves and inter-pair minimum separation constraint to refer to the constraint imposed on opposing leaves of neighboring pairs. Recall that, as shown above, it was proved that for a single pair of leaves, if the optimal plan does not satisfy the minimum separation constraint, then no plan satisfies the constraint. In this section an algorithm is presented to generate the optimal schedule for the desired profile defined over a 2-D region. The algorithm is then modified to generate schedules that satisfy the inter-pair minimum separation constraint.

An optimal schedule without the minimum separation constraint is now described. Assume n pairs of leaves. For each pair, there are m sample points. The input is represented as a matrix with n rows and m columns, where the ith row represents the desired intensity profile to be delivered by the ith pair of leaves. The Algorithm SINGLEPAIR is applied to determine the optimal plan for each of the n leaf pairs. This method of generating schedules is described in Algorithm MULTIPAIR shown below.

Algorithm MULTIPAIR
For(i=1; i≦n; i++)
Apply Algorithm SINGLEPAIR to the ith pair of leaves to obtain plan $(I_{il}, I_{ir})$ that delivers the intensity profile $I_i(x)$.
End For Lemma 4. Algorithm MULTIPAIR generates schedules that are optimal in therapy time.

An optimal algorithm with inter-pair minimum separation constraint is now described. The schedule generated by Algorithm MULTIPAIR may violate both the intra- and inter-pair minimum separation constraints. If the schedule has no violations of these constraints, the schedule is the desired optimal schedule. If there is a violation of the intra-pair constraint, then it follows from Theorem 2 that there is no schedule that is free of constraint violation. So, assume that only the inter-pair constraint is violated. All violations of the inter-pair constraint are eliminated starting from the left end, i.e., from $x_0$. To eliminate the violations, those plans of the schedule that cause the violations are modified. The schedule is scanned from $x_0$ along the positive x direction looking for the least $x_v$ at which is positioned a right leaf (say Ru) that violates the inter-pair separation constraint. After rectifying the violation at $x_v$ with respect to Ru, other violations are looked for. Since the process of eliminating a violation at $x_v$, may at times, lead to new violations at $x_j$, $x_j < x_v$, it is sometimes needed to retract a certain distance (shown as $S_{min}$) to the left, every time a modification is made to the schedule. The scanning and modification process is then restarted from the new position. The process continues until no inter-pair violations exist. Algorithm MINSEPARATION below outlines this procedure.

Algorithm MINSEPARATION
Assume no intra-pair violations exist
i. $x = x_0$
ii. While (there is an inter-pair violation) do
iii. Find the least $x_v$, $x_v \geq x$, such that a right leaf is positioned at $x_v$ and this right leaf has an inter-pair separation violation with one or both of its neighboring left leaves. Let u be the least integer such that the right leaf Ru is positioned at $x_v$ and Ru has an inter-pair separation violation. Let Lt denote the left leaf (or one of the left leaves) with which Ru has an inter-pair violation. Note that $t \in \{u-1, u+1\}$.
iv. Modify the schedule to eliminate the violation between Ru and Lt.
v. If there is now an intra-pair separation violation between Rt and Lt, no feasible schedule exists, terminate.
vi. $x = x_v - S_{min}$
vii. End While Let $M = ((I_{1l}, I_{1r}), (I_{2l}, I_{2r}), \ldots, (I_{nl}, I_{nr}))$ be the schedule generated by Algorithm MULTIPAIR for the desired intensity profile.

Let $N(p) = ((I_{1lp}, I_{1rp}), (I_{2lp}, I_{2rp}), \ldots, (I_{nlp}, I_{nrp}))$ be the schedule obtained after step (iv) of the Algorithm MINSEPARATION is applied p times to the input schedule M. Note that $M = N(0)$.

Figure 10:
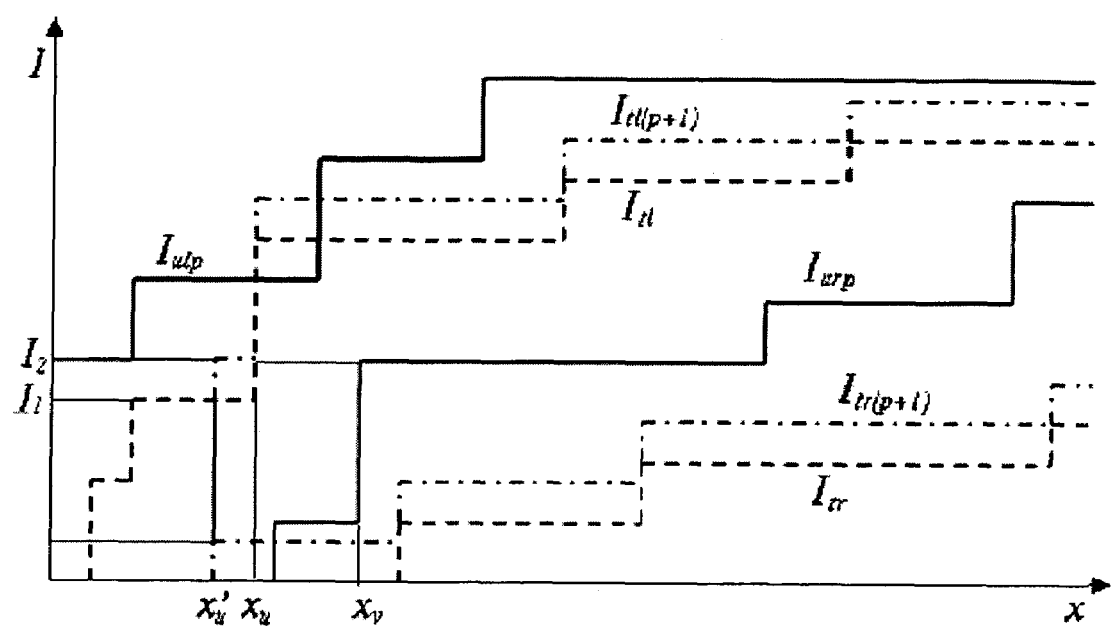
FIG. 10 illustrates the results of a leaf sequence modification process which eliminates minimum separation violations.

To illustrate the modification process to eliminate violations, FIG. 10 is provided. To simplify, only two neighboring pairs of leaves are shown in FIG. 10. Suppose that the (p+1)th violation occurs when the right leaf of pair u is positioned at $x_v$ and the left leaf of pair t, $t \in \{u-1, u+1\}$, arrives at $x_u$, $x_v - x_u < S_{min}$. Let $x_u = x_v - S_{min}$. To remove this inter-pair separation violation, $(I_{tlp}, I_{trp})$ is modified. The other profiles of $N(p)$ are not modified. The new $I_{tlp}$ (i.e., $I_{tl(p+1)}$) is defined below.

$$I_{tl(p+1)}(x) = \{I_{tlp}(x) \; x_0 \leq x < x_u$$

$$\max\{I_{tlp}(x), I_{tl}(x) + \Delta I\} \; x_u \leq x \leq x_m$$

where $\Delta I = I_{urp}(x_v) - I_{tl}(x_u) = I_2 - I_1$. $I_{tr(p+1)}(x) = I_{tl(p+1)}(x) - I_t(x)$, where $I_t(x)$ is the target profile to be delivered by the leaf pair t. Since $I_{tr(p+1)}$ differs from $I_{trp}$ for $x \geq x_u = x_v - S_{min}$ there is a possibility that $N(p+1)$ has inter-pair separation violations for right leaf positions $x \geq x_u = x_v - S_{min}$. Since none of the other right leaf profiles are changed from those of $N(p)$ and since the change in $I_{tl}$ only delays the rightward movement of the left leaf of pair t, no inter-pair violations are possible in $N(p+1)$ for $x < x_u = x_v - S_{min}$. One may also verify that since $I_{tl0}$ and $I_{tr0}$ are non-decreasing functions of x, so also are $I_{tlp}$ and $I_{trp}$, p>0.

Lemma 5. Let $F = ((I_{1l}, I_{1r}), (I_{2l}, I_{2r}), \ldots, (I_{nl}, I_{nr}))$ be any feasible schedule for the desired profile, i.e., a schedule that does not violate the intra- or inter-pair minimum separation constraints. Let S(p), be the following assertions.

i. $I_{il}(x) \geq I_{ilp}(x)$, $0 \leq i \leq n$, $x_0 \leq x \leq x_m$
ii. $I_{ir}(x) \geq I_{irp}(x)$, $0 \leq i \leq n$, $x_0 \leq x \leq x_m$ S(p) is true for $p \geq 0$.

Lemma 6. If an intra-pair minimum separation violation is detected in step (v) of MINSEPARATION, then there is no feasible schedule for the desired profile.

Figure 11A:
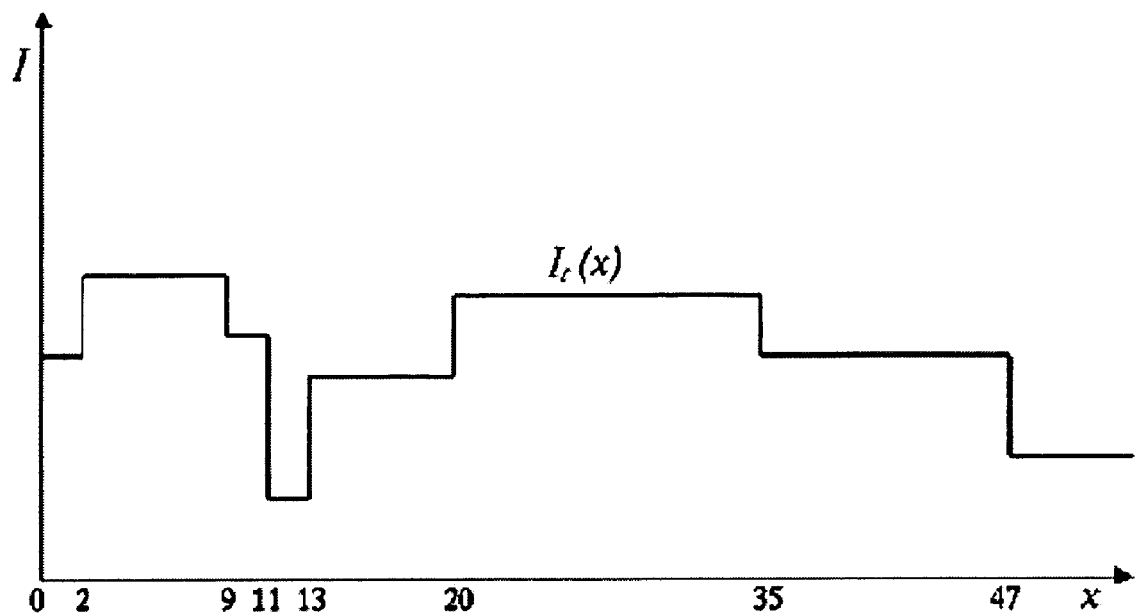
FIGS. 11(a) and (b) show intensity profiles to be delivered by adjacent leaf pairs t and t+1, respectively.
Figure 11B:
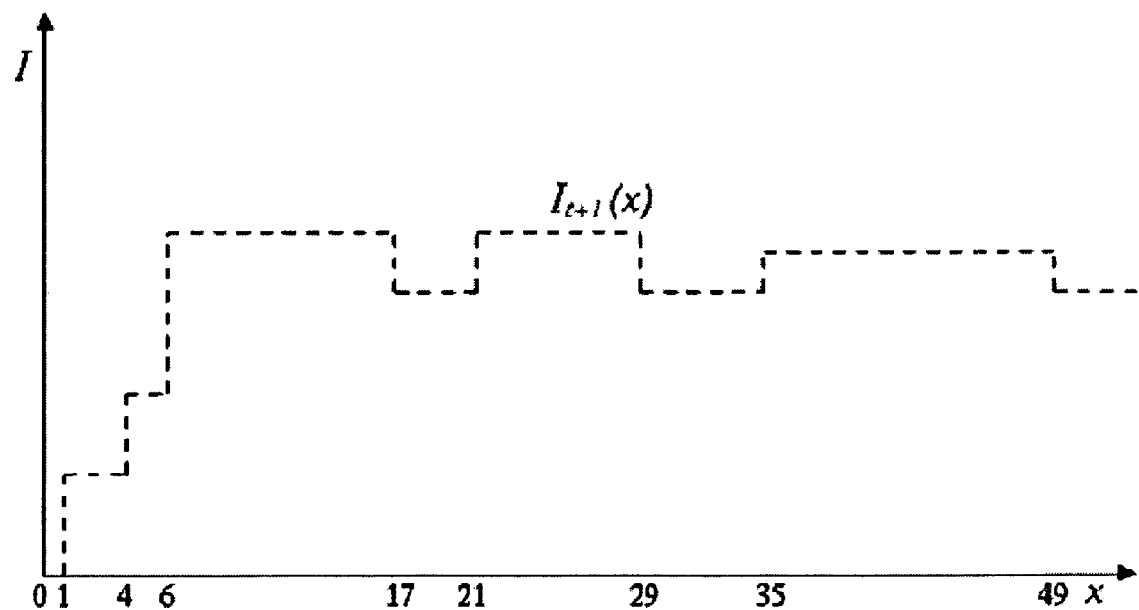
Figure 12:
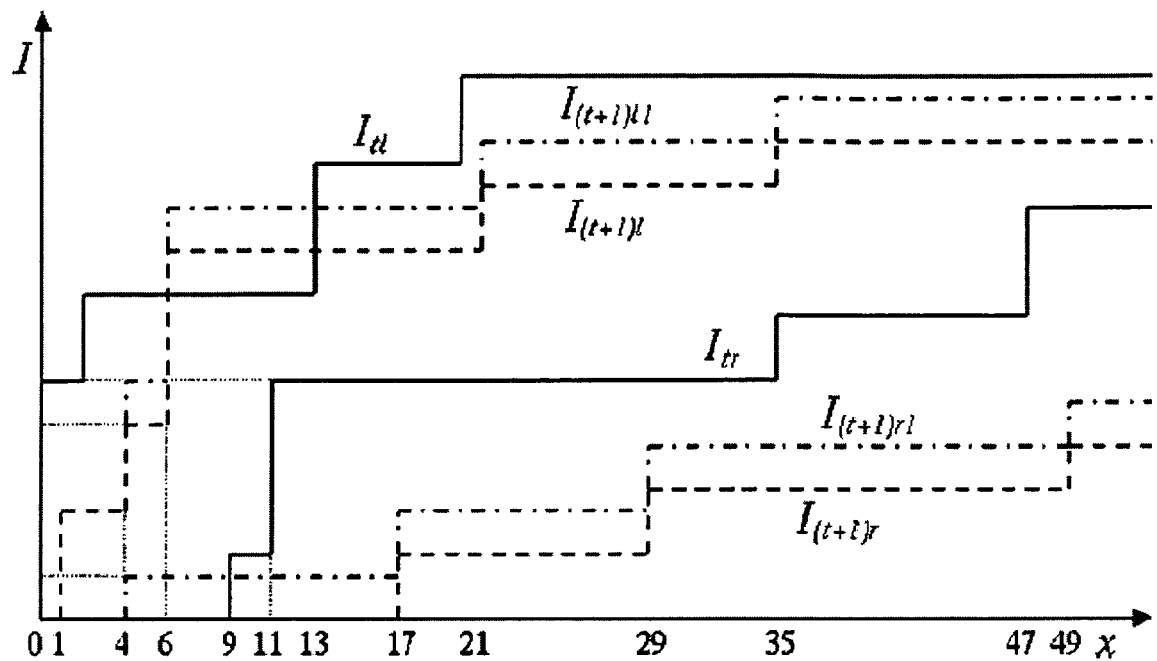
FIG. 12 shows the plans for $I_t(x)$ and $I_{t+1}(x)$ from the profiles shown in FIGS. 11(a) and (b) obtained using algorithm MULTIPAIR.

Suppose that there is a feasible schedule F and that leaf pair t has an intra-pair minimum separation violation in $N(p)$, p>0. From Lemma 5 it follows that (a) $I_{tl}(x) \geq I_{tlp}(x)$, $x_0 \leq x \leq x_m$
(b) $I_{tr}(x) \geq I_{trp}(x)$, $x_0 \leq x \leq x_m$ An instance is now described where an inter-pair minimum separation violation is detected in step (v) of the algorithm MINSEPARATION. FIGS. 11(a) and (b) show intensity profiles to be delivered by adjacent leaf pairs t and t+1, respectively. The plans for $I_t(x)$ and $I_{t+1}(x)$ are obtained using algorithm MULTIPAIR are shown in FIG. 12. Each of these plans $((I_{tl}(x), I_{tr}(x))$ and $(I_{(t+1)l}(x), I_{(t+1)r}(x)))$ is feasible, i.e., there is no intra-pair minimum separation ($S_{min} = 7$). However, when MINSEPARATION is applied (for simplicity consider leaf pairs t and t+1 in isolation), it detects an inter-pair minimum separation violation between $I_{(t+1)l}$ and $I_{tr}$, when $I_{(t+1)l}$ arrives at x=6 and $I_{tr}$ is positioned at x=11. To eliminate this violation, $I_{(t+1)l}$ is positioned at x=4 (since $11 - 4 = 7 = S_{min}$) and its profile is raised from x=4. Consequently $I_{(t+1)r}$ is also raised from x=4 resulting in the plan $(I_{(t+1)l1}(x), I_{(t+1)r1}(x))$. This modification results in an intra-pair violation for pair t+1, when $I_{(t+1)l1}$ is at x=1 and $I_{(t+1)r1}$ is at x=4. From Lemma 6, there is no feasible schedule.

For $N(p)$, $p \geq 0$ and every leaf pair j, $1 \leq j \leq n$, define $I_{jlp}(x_{-1}) = I_{jrp}(x_{-1}) = 0$, $\Delta_{jlp}(x_i) = I_{jlp}(x_i) - I_{jlp}(x_{i-1})$, $0 \leq i \leq m$ and $\Delta_{jrp}(x_i) = I_{jrp}(x_i) - I_{jrp}(x_{i-1})$, $0 \leq i \leq m$. Notice that $\Delta_{jlp}(x_i)$ gives the time (in monitor units) for which the left leaf of pair j stops at position $x_i$. Let $\Delta_{jlp}(x_i)$ and $\Delta_{jrp}(x_i)$ be zero for all $x_i$ when j=0 as well as when j=n+1.

Lemma 7. For every j, $1 \leq j \leq n$ and every i, $1 \leq i \leq m$, $$\Delta_{jlp}(x_i) \leq \max\{\Delta_{jl0}(x_i), \Delta_{(j-1)rp}(x_i + S_{min}), \Delta_{(j+1)rp}(x_i + S_{min})\} \quad (2)$$

Lemma 8. For every j, $1 \leq j \leq n$ and every i, $1 \leq i \leq m$, $$\Delta_{jrp}(x_i) = \Delta_{jlp}(x_i) - (I_j(x_i) - I_j(x_{i-1})) \quad (3)$$

where $I_j(x_{-1}) = 0$.

Notice that once a right leaf u moves past $x_m$, no separation violation with respect to this leaf is possible. Therefore, $x_v$ (see algorithm MINSEPARATION) $\leq x_m$. Hence, $\Delta_{jlp}(x_i) \leq \Delta_{jl0}(x_i)$, and $\Delta_{jrp}(x_i) \leq \Delta_{jr0}(x_i)$, $x_m - S_{min} \leq x_i \leq x_m$, $1 \leq j \leq n$. Starting with these upper bounds, which are independent of p, on $\Delta_{jrp}(x_i)$, $x_m - S_{min} \leq x_i \leq x_m$ and using Equations 2 and 3, an upper bound on the remaining $\Delta_{jlp}(x_i)$s and $elta_{jrp}(x_i)$s are computed (from right to left). The remaining upper bounds are also independent of p. Let the computed upper bound on $\Delta_{jlp}(x_i)$ be $U_{jl}(x_i)$. It follows that the therapy time for $(I_{jlp}, I_{jrp})$ is at most $T_{max}(j) = \Sigma_{0 \leq i \leq m} U_{jl}(x_i)$. Therefore, the therapy time for $N(p)$ is at most $T_{max} = \max_{1 \leq j \leq n}\{T_{max}(j)\}$.

Theorem 6. The following are true of Algorithm MIN-SEPARATION:
a. The algorithm terminates.
b. When the algorithm terminates in Step (v), there is no feasible schedule.
c. Otherwise, the schedule generated is feasible and is optimal in therapy time.

Corollary 3. When $S_{min}=0$, the Algorithm Minseparation always generates an optimal feasible schedule.

Example 2

Optimal Sequencing of Dynamic Multileaf Collimators

The geometry and coordinate system used in this Example are the same as shown in FIG. 4. The delivery of intensity map produced by the optimizer is considered. It is important to note that the intensity map from the optimizer is always a discrete matrix. The spatial resolution of this matrix is similar to the smallest beamlet size. The beamlet size typically ranges from 5–10 mm. Most leaf sequencing algorithms for DMLC delivery published in literature and implemented in commercial software first convert the discrete intensity matrix into a piecewise continuous function with linear interpolation between the intensity values thus yielding smooth and continuous intensity map. This is believed to be unnecessary if the leaf sequencing algorithm can exactly reproduce the optimized intensity map. The leaf sequencing algorithm described herein is designed to reproduce exactly the same intensity map as it comes out of the optimizer. This ensures an exact reproduction of the planned dose distribution. With this consideration, let I(x) be the desired intensity profile along x axis. The discretized profile from the optimizer gives the intensity values at sample points $x_0, x_1, \ldots, x_m$.

It is assumed that the sample points are uniformly spaced and that $\Delta x = x_{i+1} - x_i$, $0 \leq i < m$. I(x) is assigned the value $I(x_i)$ for $x_i \leq x < x_{i+1}$, for each i. Now, $I(x_i)$ is our desired intensity profile, i.e., $I(x_i)$ is a measure of the number of MUs for which $x_i$, $0 \leq i < m$, needs to be exposed.

FIG. 5(b) shows a discretized profile, which is the output from the optimizer at discrete sample points $x_0, x_1, \ldots, x_m$. In this Example, this profile is delivered with Dynamic Multileaf Collimation (DMLC).

Figure 13:
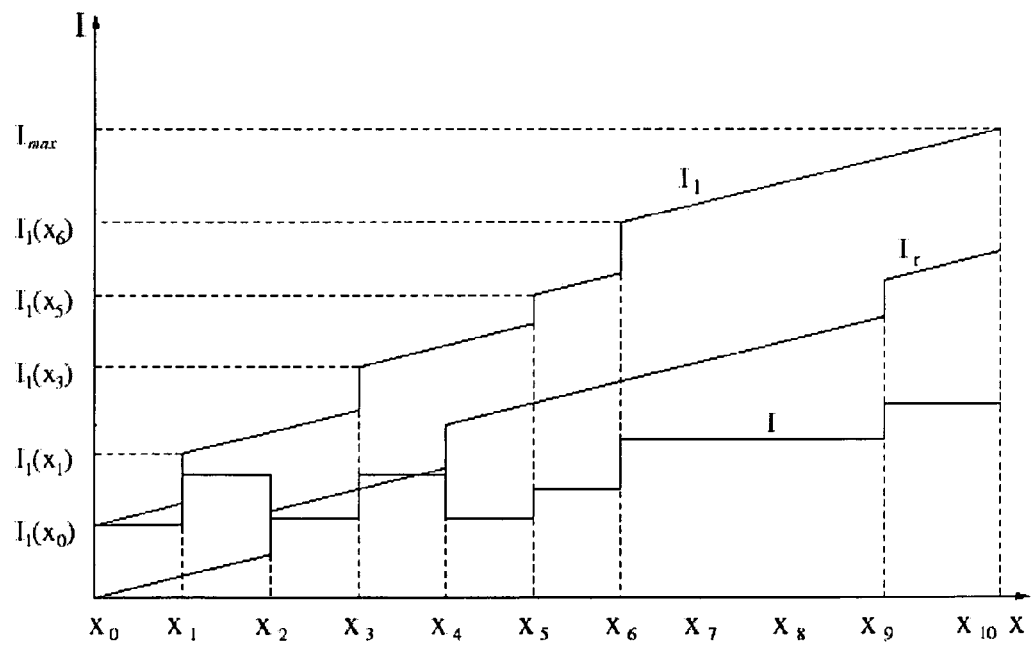
FIG. 13 illustrates a leaf trajectory plan obtained using Algorithm DMLC-SINGLEPAIR.

In this analysis it will be assumed that $I(x_0)>0$ and $I(x_m)>0$ and that when the beam delivery begins the leaves can be positioned anywhere. It is also assumed that the leaves can move with any velocity v, $-v_{max} \leq v \leq v_{max}$, where $v_{max}$ is the maximum allowable velocity of the leaves. FIG. 13 illustrates an exemplary leaf trajectory during DMLC delivery. In this Example, the leaves move from left to right. Let $I_l(x_i)$ and $I_r(x_i)$, respectively, denote the amount of Monitor Units (MUs) delivered when the left and right leaves leave position $x_i$. Consider the motion of the left leaf. The left leaf begins at $x_0$ and remains here until $I_l(x_0)$ MUs have been delivered. At this time the left leaf leaves $x_0$ and is moved to $x_1$, where it remains until $I_l(x_1)$ MUs have been delivered. The left leaf then moves to $x_3$ where it remains until $I_l(x_3)$ MUs have been delivered. At this time, the left leaf is moved to $x_5$, where it remains until $I_l(x_5)$ MUs have been delivered. Then it moves to $x_6$, where it remains until $I_l(x_6)$ MUs have been delivered. The final movement of the left leaf is to $x_{10}$. The left leaf arrives at $x_{10}$ when $I_{max}$ MUs have been delivered. At this time the machine is turned off. The total therapy time, $TT(I_l, I_r)$, is the time needed to deliver $I_{max}$ MUs. The right leaf starts at $x_0$ and begins to move rightaway till it reaches $x_2$; leaves $x_2$ when $I_r(x_2)$ MUs have been delivered; leaves $x_4$ when $I_r(x_4)$ MUs have been delivered, and so on. Note that the machine is on throughout the treatment. All MUs that are delivered along a radiation beam along $x_i$ before the left leaf passes $x_i$ fall on it. Similarly, all Mus that are delivered along a radiation beam along $x_i$ before the right leaf passes $x_i$ are blocked by the leaf. So the net amount of MUs delivered at a point is given by $I_l(x_i) - I_r(x_i)$, which must be the same as the desired profile $I(x_i)$.

Theorem 1. The following are true of every leaf pair trajectory that delivers a discrete profile:
(a) The left leaf must reach $x_0$ at some time.
(b) The right leaf must reach $x_m$ at some time.
(c) The left leaf must reach $x_m$ at some time.
(d) The right leaf must reach $x_0$ at some time.

As noted earlier, the velocity of leaves cannot exceed some maximum limit (say $v_{max}$) in practice. This implies that the leaf profile cannot be horizontal at any point. From FIG. 13, it can be seen that the time needed for a leaf to move from $x_i$ to $x_{i+1}$ is $\geq (x_{i+1} - x_i)/v_{max}$. If $\Phi$ is the flux density of MUs from the source, the number of MUs delivered in this time along a beam is $\geq \Phi^*(x_{i+1}-x_i)/v_{max}$. So, $I_l(x_{i+1}) - I_l(x_i) \geq \Phi^*(x_{i+1}-x_i)/v_{max} = Phi^*\Delta x/v_{max}$. The same is true for the right leaf profile $I_r$.

An optimal unidirectional algorithm for one pair of leaves is now described. When the movement of leaves is restricted to only one direction, both the left and right leaves move along the positive x direction, from left to right. Once the desired intensity profile, $I(x_i)$ is known, the problem becomes that of determining the individual intensity profiles to be delivered by the left and right leaves, $I_l$ and $I_r$ such that:

$$I(x_i) = I_l(x_i) - I_r(x_i), \ 0 \leq i \leq m \quad (1)$$

$I_l$ and $I_r$ are subject to the maximum velocity constraint. $(I_l, I_r)$ is referred to as the treatment plan (or simply plan) for I. Once the plan is obtained, the movement of both left and right leaves during the therapy will be determined. For each i, the left leaf can be allowed to pass $x_i$ when the source has delivered $I_l(x_i)$ MUs. Also, it is possible to allow the right leaf to pass $x_i$ when the source has delivered $I_r(x_i)$ MUs. In this manner, unidirectional leaf movement profiles for a plan are determined. Some observations about the leaf profiles are made below.

Theorem 2. In every unidirectional plan the leaves begin at $x_0$ and end at $x_m$. A proof of this theorem follows from Theorem 1 and the unidirectional constraint.

Lemma 1. In the region between each pair of successive sample points, say $x_i$ and $x_{i+1}$, both leaf profiles maintain the same shape, i.e., one is merely a vertical translation of the other.

Lemma 2. In an optimal plan, both leaves must move at $v_{max}$ between every successive pair of sample points they move across.

Corollary 1. In an optimal plan, no leaf stops at an x that is not one of the $x_i$s. From Equation 1, it can be seen that one way to determine $I_l$ and $I_r$ from the given target profile I is to begin from $x_0$; set $I_l(x_0) = I(x_0)$ and $I_r(x_0) = 0$; examine the remaining $x_i$s to the right; increase $I_l$ at $x_i$ whenever I increases and by the same amount (in addition to the minimum increase imposed by the maximum velocity constraint); and similarly increase $I_r$ whenever I decreases. This can be done till $x_m$ is reached. So the treatment begins with the leaves positioned at the leftmost sample point and ends with the leaves positioned at the rightmost sample point. Once $I_l$ and $I_r$ are determined the leaf movement profiles are obtained as explained earlier. Note that leaves are moved at the maximum velocity $v_{max}$ whenever they are to be moved.

Figure 14:
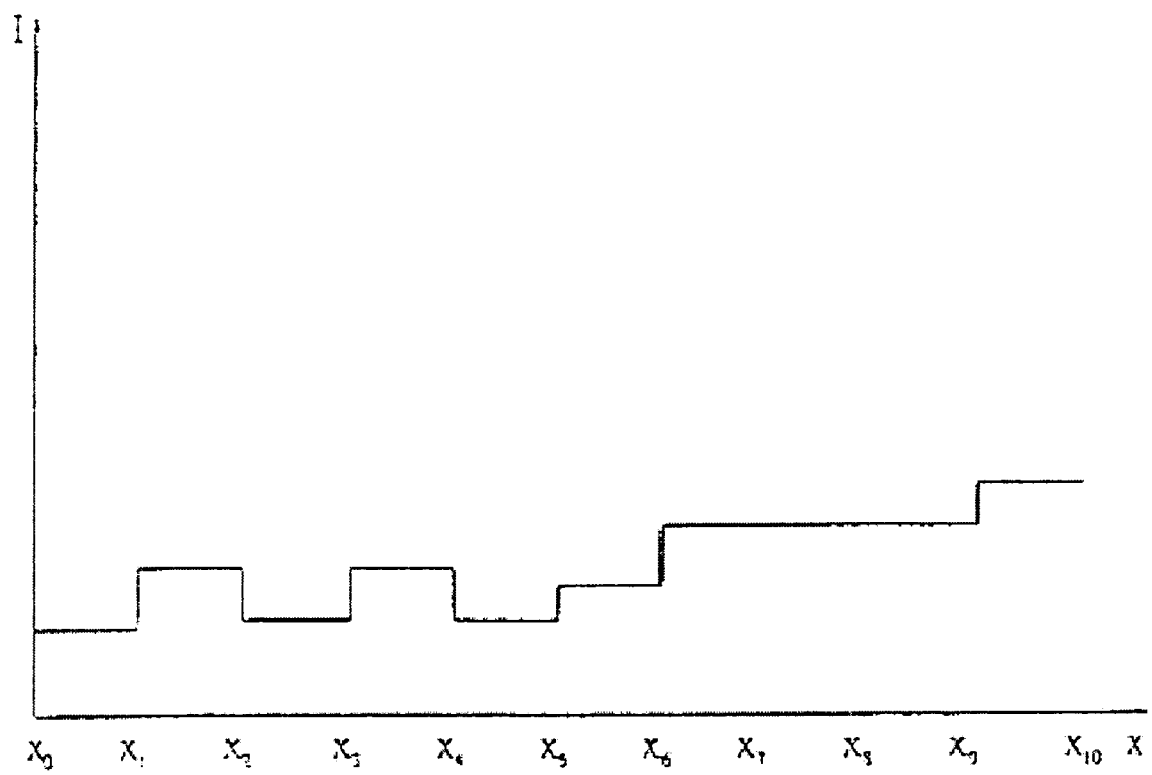
FIG. 14 shows a profile using Algorithm DMLC-SINGLEPAIR.

The resulting Algorithm DMLC-SINGLEPAIR is shown below. FIG. 14 shows a profile I and FIG. 13 shows the corresponding plan $(I_l, I_r)$ obtained using Algorithm DMLC-SINGLEPAIR.

Algorithm DMLC-SINGLEPAIR
$I_l(x_0) = I(x_0)$
$I_r(x_0) = 0$
For j=1 to m do
If $(I(x_j) \geq I(x_{j-1}))$
$I_l(x_j) = I_l(x_{j-1}) + I(x_j) - I(x_{j-1}) + \Phi^* \Delta x / v_{max}$
$I_r(x_j) = I_r(x_{j-1}) + \Phi^* \Delta x / v_{max}$
Else
$I_r(x_j) = I_r(x_{j-1}) + I(x_{j-1}) - I(x_j) + \Phi^* \Delta x / v_{max}$
$I_l(x_j) = I_l(x_{j-1}) + \Phi^* \Delta x / v_{max}$
End for It has been shown that the Algorithm DMLC-SINGLEPAIR obtains plans that are optimal in therapy time. However, the proof is complex and indirect. A simpler and direct proof is provided below.

Theorem 3. Algorithm DMLC-SINGLEPAIR obtains plans that are optimal in therapy time.

Corollary 2. Let $I(x_i)$, $0 \leq i \leq m$ be a desired profile. Let $I_l(x_i)$ and $I_r(x_i)$, $0 \leq i \leq m$ be the left and right leaf profiles generated by Algorithm DMLC-SINGLEPAIR. $I_l(x_i)$ and $I_r(x_i)$, $0 \leq i \leq m$ define optimal therapy time unidirectional left and right leaf profiles for $I(x_i)$, $0 \leq i \leq m$.

In the remainder of this section, $(I_l, I_r)$ is the optimal treatment plan generated by Algorithm DMLC-SINGLEPAIR for the desired profile I.

The following observations are made about the optimal treatment plan $(I_l, I_r)$ generated using Algorithm DMLC-SINGLEPAIR.

Lemma 3. At most one of the leaves stops at each $x_i$.

Lemma 4. Let $(I_L, I_R)$ be any treatment plan for I.
(a) $\Delta(x_i) = I_L(x_i) - I_l(x_i) = I_R(x_i) - I_r(x_i) \geq 0$, $0 \leq i \leq m$.
(b) $\Delta(x_i)$ is a non-decreasing function.

Corollary 3. Let $\Lambda_l(x_i)(\Lambda_r(x_i))$ and $\Lambda_L(x_i)(\Lambda_R(x_i))$, respectively, denote the amount of time for which the left (right) leaf stops at $x_i$ in plans $(I_l, I_r)$ and $(I_L, I_R)$. Then
(a) $\Lambda_L(x_i) \geq \Lambda_l(x_i)$.
(b) $\Lambda_R(x_i) \geq \Lambda_r(x_i)$.

Some MLCs have a minimum separation constraint that requires the left and right leaves to maintain a minimum separation $S_{min}$ at all times during the treatment. Notice that in the plan generated by Algorithm DMLC-SINGLEPAIR, the two leaves start and end at the same point. Accordingly, they are in contact at $x_0$ and $x_m$. When $S_{min} > 0$, the minimum separation constraint is violated at $x_0$ and $x_m$. In order to overcome this problem, the Algorithm DMLC-SINGLEPAIR is modified to guarantee minimum separation between the leaves in the vicinity of the end points ($x_0$ and $x_m$). In particular, the left leaf is permitted to be initially positioned at a point $x_{0'} = x_0 - S_{min}$ and the right leaf to be finally positioned at $x_{m'} = x_m + S_{min}$. The only changes made relative to Algorithm DMLC-SINGLEPAIR are for the movement of the left leaf from $x_{0'}$ to $x_0$ and for the right leaf from $x_m$ to $x_{m'}$. The movement of the left leaf from $x_{0'}$ to $x_0$ (and a symmetric definition for the right leaf from $x_m$ to $x_{m'}$) is defined to be such that it maintains a distance of exactly $S_{min}$ from the right leaf at all times. Once the left leaf reaches $x_0$ it follows the trajectory as before. While this modification results in the exact profile being delivered between $x_0$ and $x_m$ it also results in some undesirable exposure to the intervals $(x_{0'}, x_0)$ and $(x_m, x_{m'})$. In the remainder of this section exposures of this kind permissible will be considered permissible, provided the exact profile is delivered between $x_0$ and $x_m$. Note that for most commercially available accelerators, undesirable exposure to the intervals $(x_{0'}, x_0)$ and $(x_m, x_{m'})$ can be avoided by positioning the back-up jaws at $x_0$ and $x_m$ respectively. However, a difficulty arises when the number of monitor units delivered at the time the left leaf reaches $x_0$ in this new plan (call it $(I_l, I_r)$) is greater than $I_l(x_0)$. This would prevent using the old plan from $x_0$ to $x_m$, since the leaf cannot pass $x_0$ before it arrives there. However, that if the left leaf were to arrive at $x_0$ any earlier, it would be too close to the right leaf. In the discussion that follows it is shown that in this and other cases where the original plan violates the constraint, there are no feasible solutions that deliver exactly the desired profile between $x_0$ and $x_m$, while permitting exposure outside this region. The modified algorithm, which is referred to herein as DMLC-MINSINGLEPAIR, is described below. Note that the therapy time of the plan produced by DMLC-MINSINGLEPAIR is the same as that of the plan produced by DMLC-SINGLEPAIR. Therefore, the modified plan is optimal in therapy time.

Algorithm DMLC-MINSINGLEPAIR
1. Apply Algorithm DMLC-SINGLEPAIR
2. Modify the profile of the left leaf from $x_{0'}$ to $x_0$ and the right leaf from $x_m$ to $x_{m'}$, to maintain a minimum interleaf distance of $S_{min}$. Call this profile $(I_l, I_r)$.
3. If the number of MUs delivered when the left leaf arrives at $x_0$ is greater than $I_l(x_0)$ there is no feasible solution. End.
4. Else output $(I_l, I_r)$. There is a feasible solution only if $(I_l, I_r)$ is feasible.

Theorem 4. (a) $S_{min} * \Phi / v_{max} > I_l(x_0)$ or (b) If the plan $(I_l, I_r)$ generated by DMLC-MINSINGLEPAIR violates the minimum separation constraint, then there is no plan for I that does not violate the minimum separation constraint.

The separation between the leaves is determined by the difference in x values of the leaves when the source has delivered a certain amount of MUs. The minimum separation of the leaves is the minimum separation between the two profiles. This minimum separation is referred to herein as $S_{ud-min}$. When the optimal plan obtained using Algorithm DMLC-SINGLEPAIR is delivered, the minimum separation is $S_{ud-min(opt)}$.

Corollary 4. Let $S_{ud-min(opt)}$ be the minimum leaf separation in the plan $(I_l, I_r)$. Let $S_{ud-min}$ be the minimum leaf separation in any (not necessarily optimal) given unidirectional plan. $S_{ud-min} \leq S_{ud-min(opt)}$.

Theorem 5. If Algorithm DMLC-MINSINGLEPAIR terminates in Step 3, then there is no plan for I that does not violate the minimum separation constraint.

The DMLC leaf sequence is now compared with small sequencing.

Lemma 5. Let the minimum separation between the leaves in the optimal SMLC plan be $S_{s-min}$. Let the minimum leaf separation in the plan generated by algorithm DMLC-MINSINGLEPAIR be $S_{d-min}$. Then $S_{d-min} \leq S_{s-min}$. The following result immediately follows and can be easily verified.

Corollary 5. All profiles that have feasible plans using DMLC have feasible plans using SMLC. There exist profiles for which there are feasible plans using SMLC, but no feasible plans using DMLC.

Figure 15:
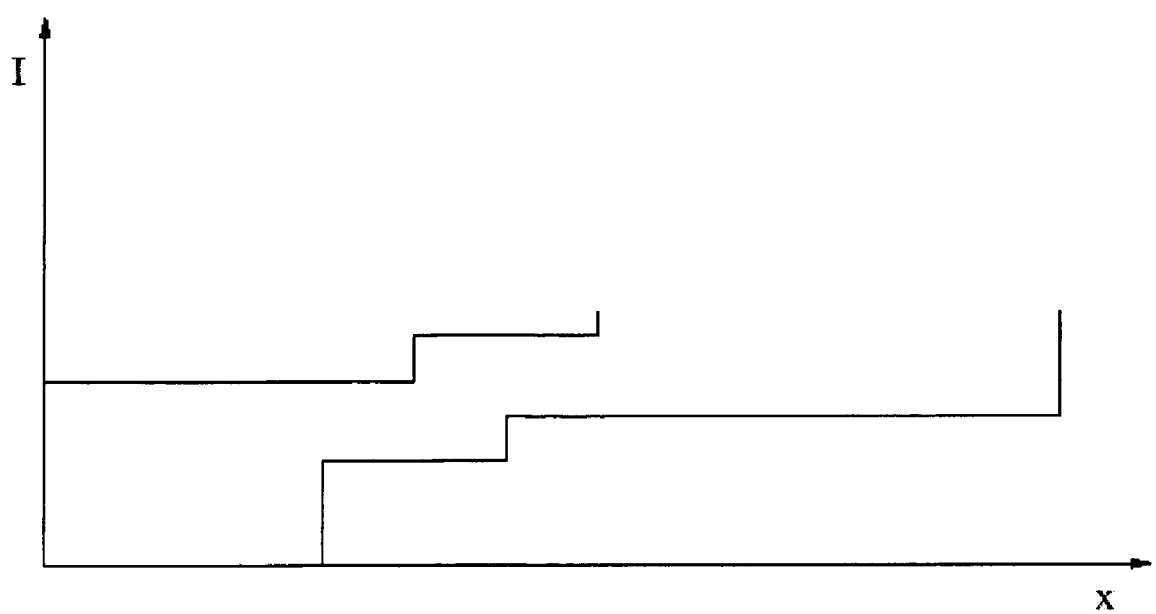
FIG. 15 shows a SMLC plan of a feasible profile.
Figure 16:
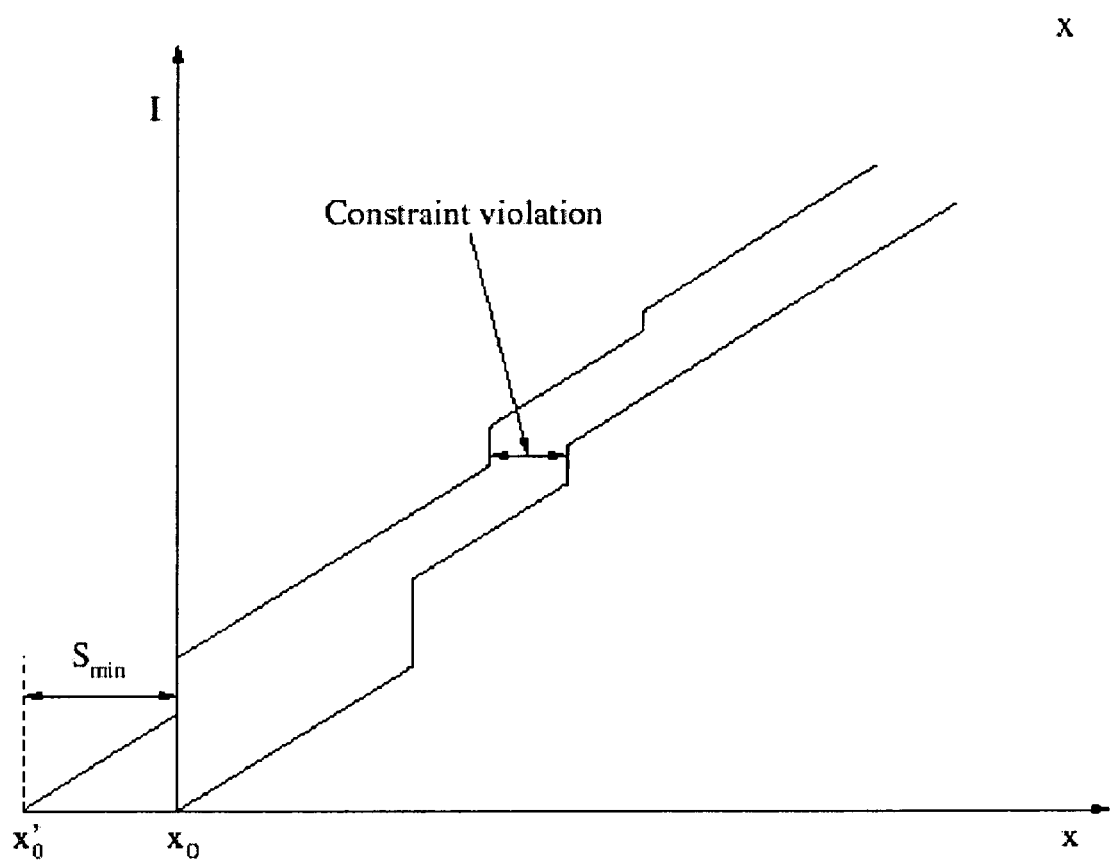
FIG. 16 shows the DMLC plan corresponding to the SMLC plan shown in FIG. 15 using Algorithm DMLC-MINSINGLEPAIR. The plan is infeasible.

FIG. 15 shows a SMLC plan for a feasible profile. The corresponding DMLC plan obtained using Algorithm DMLC-MINSINGLEPAIR shown in FIG. 16 is seen to be infeasible.

Beam delivery when bi-directional movement of leaves is permitted using the invention is now described. The effects of relaxing the unidirectional movement constraint on the efficiency of treatment plan is considered. For a given leaf (left or right) movement profile any x-coordinate is classified as follows. Draw a vertical line at x. If the line cuts the leaf profile exactly x is referred to as a unidirectional point of that leaf profile. If the line cuts the profile more than once, x is referred to as a bi-directional point of that profile. A leaf movement profile that has at least one bi-directional point is a bi-directional profile. All profiles that are not bi-directional are unidirectional profiles. Any profile can be partitioned into segments such that each segment is a unidirectional profile. When the number of such partitions is minimal, each partition is called a stage of the original profile. Thus unidirectional profiles consist of exactly one stage while bi-directional profiles always have more than one stage.

Figure 17:
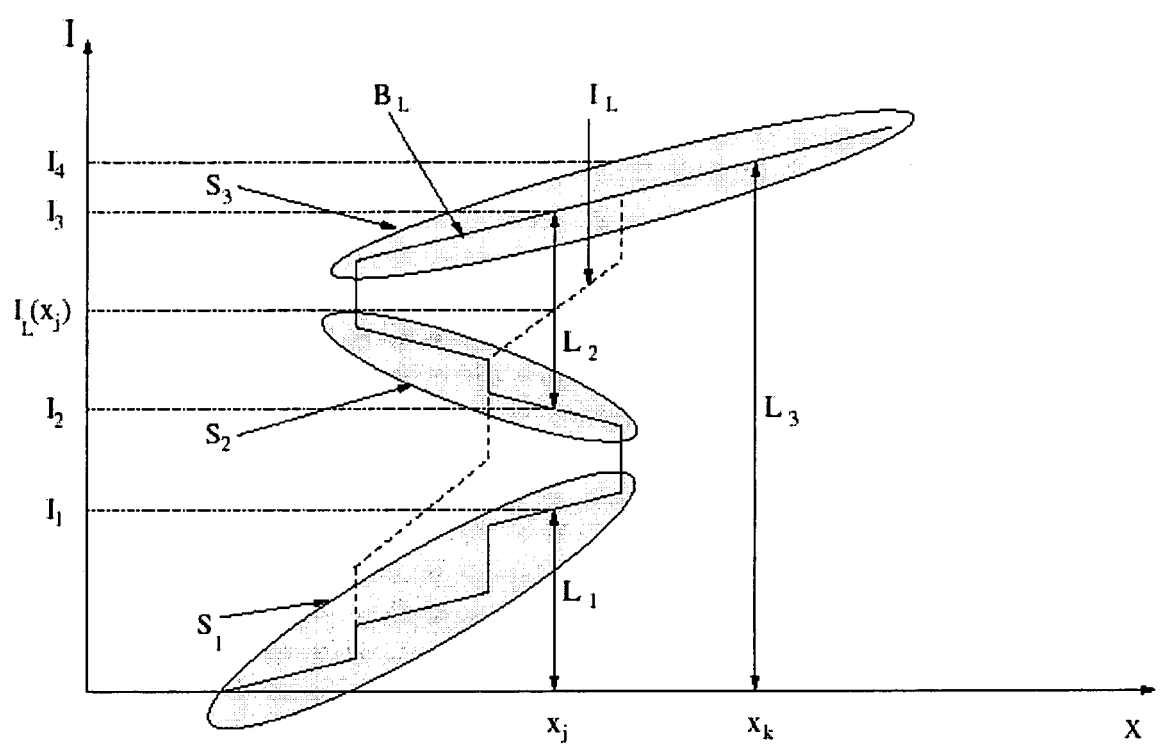
FIG. 17 shows a bi-directional leaf movement profile.

FIG. 17 shows a bi-directional leaf movement profile, $B_L$, which shows the position of the left leaf as a function of the amount of MUs delivered by the source. The movement profile of this leaf consists of stages $S_1, S_2$ and $S_3$. In stages $S_1$ and $S_3$ the leaf moves from left to right while in stage $S_2$ the leaf moves from right to left. $x_j$ is a bi-directional point of $B_L$. Let $I_L$ be the intensity profile corresponding to the leaf movement profile $B_L$. $I_L(x)$ gives the number of MUs delivered at x using movement profile $B_L$. The amount of MUs delivered at $x_j$ is $I_1+I_2$. In stage $S_1$, when $I_1$ amount of MUs have been delivered, the leaf passes $x_j$. Now, no MU is delivered at $x_j$ till the leaf passes over $x_j$ in $S_2$. Further, $I_3-I_2$ MUs are delivered to $x_j$ in stages $S_2$ and $S_3$. Thus, $I_l(x_j)=L_1+L_2$, where $L_1=I_1$ and $L_2=I_3-I_2$. $x_k$ is a unidirectional point of $B_L$. The MUs delivered at $x_k$ are $L_3=I_4$. Note that the intensity profile $I_L$ is different from the leaf movement profile $B_L$, unlike in the unidirectional case.

Lemma 6. Let $I_L$ and $I_R$ be the intensity profiles corresponding to the bi-directional leaf movement profile pair $(B_L, B_R)$ (i.e., $B_L$ and $B_R$ are, respectively, the left and right leaf movement profiles). Let $I(x_i)=I_L(x_i)-I_R(x_i)$, $0 \leq i \leq m$, be the intensity profile delivered by $(B_L, B_R)$. Then (a) $I_L(x_{i+1}) \geq I_L(x_i) + \Phi^* \Delta x / v_{max}$.

(b) $I_R(x_{i+1}) \geq I_R(x_i) + \Phi^* \Delta x / v_{max}$.

From Lemma 6 it is noted that every bi-directional leaf movement profile $(B_L, B_R)$ delivers an intensity profile $(I_L, I_R)$ that satisfies the maximum velocity constraint. Hence, $(I_L, I_R)$ is deliverable using a unidirectional leaf movement profile. This profile is referred to herein as the unidirectional leaf movement profile that corresponds to the bi-directional profile. Thus every bi-directional leaf movement profile has a corresponding unidirectional leaf profile that delivers the same amount of MUs at each $x_i$ as does the bi-directional profile.

Theorem 6. The unidirectional treatment plan constructed by Algorithm DMLC-SINGLEPAIR is optimal in therapy time even when bi-directional leaf movement is permitted.

Incorporation of the minimum separation constraint will now be described. Let $U_l$ and $U_r$ be unidirectional leaf movement profiles that deliver the desired profile $I(x_i)$. Let $B_l$ and $B_r$ be a set of bi-directional left and right leaf profiles such that $U_l$ and $U_r$ correspond to $B_l$ and $B_r$ respectively, i.e., $(B_l, B_r)$ delivers the same plan as $(U_l, U_r)$. This is called the minimum separation of leaves in this bi-directional plan $(B_l, B_r)$ $S_{bd-min}$. $S_{bd-min}$ is the minimum separation of leaves in $(U_l, U_r)$.

Theorem 7. $S_{bd-min} \leq S_{ud-min}$ for every bi-directional leaf movement profile pair $(B_l, B_r)$ and its corresponding unidirectional profile $(U_l, U_r)$.

Theorem 8. If the optimal unidirectional plan $(I_l, I_r)$ violates the minimum separation constraint, then there is no bi-directional movement plan that does not violate the minimum separation constraint.

In a practical application, it is needed to deliver intensity profiles defined over a 2-D region. Multi-Leaf Collimators (MLCs) are used to deliver such profiles. An MLC is composed of multiple pairs of leaves with parallel axes. Referring again to FIG. 9, FIG. 9 shows an MLC that has three pairs of leaves—(L1,R1),(L2,R2) and (L3,R3). L1,L2, L3 are left leaves and R1,R2,R3 are right leaves. Each pair of leaves is controlled independently. If there are no constraints on the leaf movements, The desired profile is divided into a set of parallel profiles defined along the axes of the leaf pairs. Each leaf pair i then delivers the plan for the corresponding intensity profile $I_i(x)$. The set of plans of all leaf pairs forms the solution set. This set is referred to as the treatment schedule (or simply schedule).

In practical situations, however, there are constraints on the movement of the leaves. As discussed earlier, the minimum separation constraint requires that opposing pairs of leaves be separated by at least some distance ($S_{min}$) at all times during beam delivery. In some MLCs this constraint is applied not only to opposing pairs of leaves, but also to opposing leaves of neighboring pairs. For example, in FIG. 9, L1 and R1, L2 and R2, L3 and R3, L1 and R2, L2 and R1, L2 and R3, L3 and R2 are pairwise subject to the constraint. The term intra-pair minimum separation constraint is used to refer to the constraint imposed on an opposing pair of leaves and inter-pair minimum separation constraint to refer to the constraint imposed on opposing leaves of neighboring pairs. The inter-pair minimum separation constraint with $S_{min}=0$ is of special interest and is referred to as the interdigitation constraint. Recall that, above it was proven that for a single pair of leaves, if the optimal plan does not satisfy the minimum separation constraint, then no plan satisfies the constraint. In this section an algorithm is disclosed which generates the optimal schedule for the desired profile defined over a 2-D region. The algorithm can be modified to generate schedules that satisfy the interdigitation constraint. It is noted that in the discussion on single pair of leaves, it was assumed that $I(x_0)>0$ and that $I(x_m)>0$. However, with multiple leaf pairs, the first and last sample points with non-zero intensity levels could be different for different pairs. Hence, this assumption will no longer be made.

Assume n pairs of leaves. For each pair, there are m sample points. The input is represented as a matrix with n rows and m columns, where the ith row represents the desired intensity profile to be delivered by the ith pair of leaves. The Algorithm DMLC-SINGLEPAIR is applied to determine the optimal plan for each of the n leaf pairs. This method of generating schedules is described in Algorithm DMLC-MULTIPAIR shown below. Note that since $x_0$, $x_m$ are not necessarily non-zero for any row, $x_0$ is replaced by $x_l$ and $x_m$ is replaced by $x_g$ in Algorithm DMLC-SINGLEPAIR for each row, where $x_l$ and $x_g$, respectively, denote the first and last non-zero sample points of that row. Also, for rows that contain only zeroes, the plan simply places the corresponding leaves at the rightmost point in the field (call it $x_{m+1}$).

Lemma 7. Algorithm DMLC-MULTIPAIR generates schedules that are optimal in therapy time.

Algorithm DMLC-MULTIPAIR

For(i=1; i≤n; i++)

Apply Algorithm DMLC-SINGLEPAIR to the ith pair of leaves to obtain plan $(I_{il}, I_{ir})$ that delivers the intensity profile $I_i(x)$.

End For

The schedule generated by Algorithm DMLC-MULTIPAIR may violate the interdigitation constraint. Note that no intra-pair constraint violations can occur for $S_{min}=0$. Accordingly, the interdigitation constraint is essentially an inter-pair constraint. If the schedule has no interdigitation constraint violations, it is the desired optimal schedule. If there are violations in the schedule, all violations of the interdigitation constraint can be eliminated starting from the left end, i.e., from $x_0$. To eliminate the violations, plans of the schedule that cause the violations are modified. The schedule from $x_0$ along the positive x direction is scanned looking for the least $x_v$ at which is positioned a right leaf (say $R_u$) that violates the inter-pair separation constraint. After rectifying the violation at $x_v$ with respect to $R_u$, other violations are looked for. Since the process of eliminating a violation at $x_v$, may at times, lead to new violations involving right leaves positioned at $x_v$, it is preferred to search afresh from $x_v$ every time a modification is made to the schedule. The scanning and modification process is continued until no interdigitation violations exist. Algorithm DMLC-INTERDIGITATION shown below discloses the procedure.

Algorithm DMLC-INTERDIGITATION i. $x=x_0$
ii. While (there is an interdigitation violation) do
iii. Find the least $x_v$, $x_v \geq x$, such that a right leaf is positioned at $x_v$ and this right leaf has an interdigitation violation with one or both of its neighboring left leaves. Let u be the least integer such that the right leaf $R_u$ is positioned at $x_v$ and $R_u$ has an interdigitation violation. Let $L_t$ denote the left leaf with which $R_u$ has an interdigitation violation. Note that $t \in \{u-1, u+1\}$. In case $R_u$ has violations with two adjacent left leaves, let $t=u-1$.
iv. Modify the schedule to eliminate the violation between $R_u$ and $L_t$.
v. $x=x_v$
vi. End While Let $M=((I_{1l}, I_{1r}), (I_{2l}, I_{2r}), \ldots, (I_{nl}, I_{nr}))$ be the schedule generated by Algorithm DMLC-MULTIPAIR for the desired intensity profile.

Let $N(p)=((I_{1lp}, I_{1rp}), (I_{2lp}, I_{2rp}), \ldots, (I_{nlp}, I_{nrp}))$ be the schedule obtained after Step (iv) of Algorithm DMLC-INTERDIGITATION is applied p times to the input schedule M. Note that $M=N(0)$.

To illustrate the modification process other examples are presented. There are two types of violations that may occur. They are called Type 1 and Type 2 violations and the corresponding modifications Type 1 and Type 2 modifications herein. To simplify, only two neighboring pairs of leaves are shown. Suppose that the (p+1)th violation occurs between the right leaf of pair u, which is positioned at $x_v$, and the left leaf of pair t, $t \in \{u-1, u+1\}$.

Figure 18:
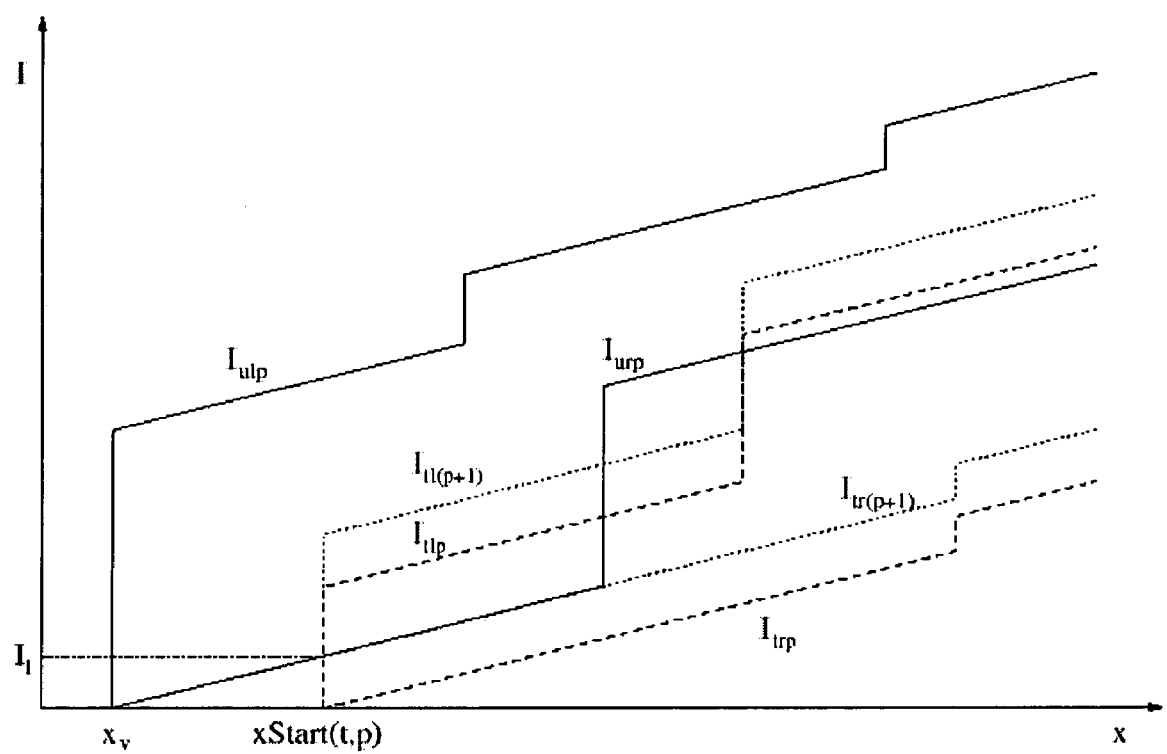
FIG. 18 illustrates "type 1" violations.

In a Type 1 violation, the left leaf of pair t starts its sweep at a point $xStart(t,p) > x_v$ (see FIG. 18). To remove this interdigitation violation, modify $(I_{tlp}, I_{trp})$ to $(I_{tl(p+1)}, I_{tr(p+1)})$ as follows. The leaves of pair t are allowed to start at $x_v$ and move them at the maximum velocity $v_{max}$ towards the right, till they reach $xStart(t,p)$. Let the number of MUs delivered when they reach $xStart(t,p)$ be $I_1$. Raise the profiles $I_{tlp}(x)$ and $I_{trp}(x)$, $x \geq xStart(t,p)$, by an amount $I_1 = \Phi*(xStart(t,p) - x_v)/v_{max}$. The result;

$I_{tl(p+1)}(x) = \{\Phi*(x-x_v)/v_{max} \; x_v \leq x < xStart(t,p)$ $I_{tlp}(x) + I_1 \; x \geq xStart(t,p)$ $I_{tr(p+1)}(x) = I_{tl(p+1)}(x) - I_t(x)$, where $I_t(x)$ is the target profile to be delivered by the leaf pair t.

Figure 19:
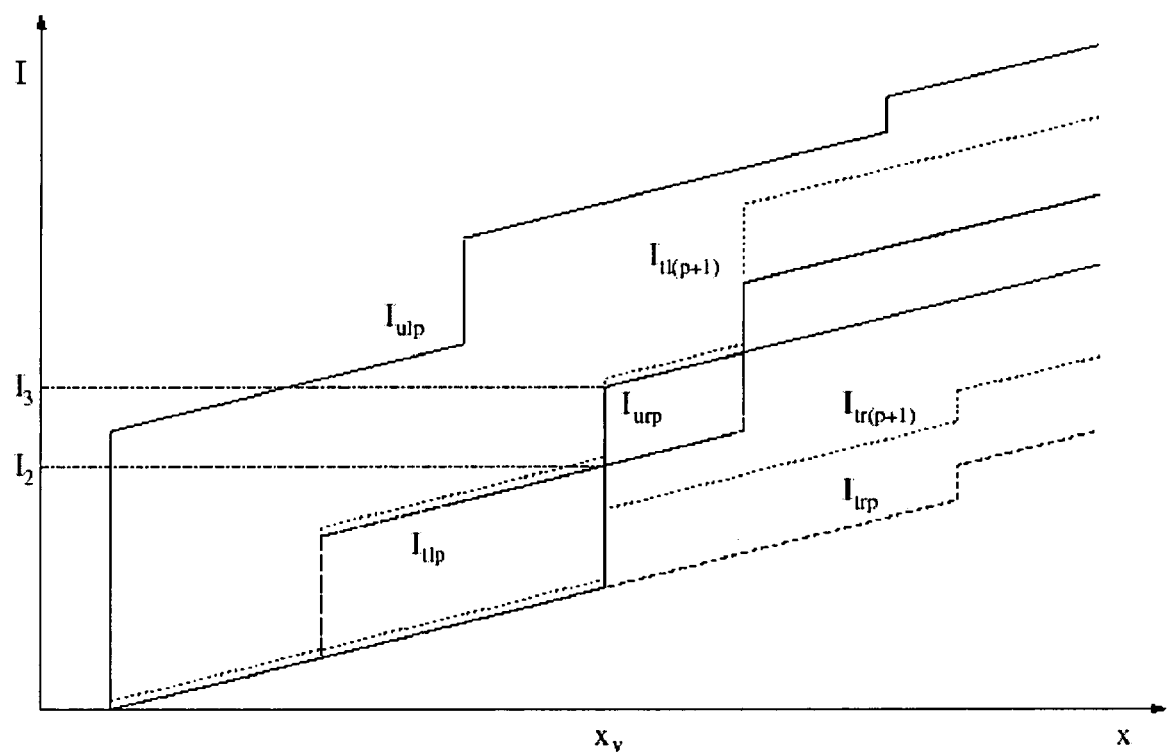
FIG. 19 illustrates "type 2" violations.

A Type 2 violation occurs when the left leaf of pair t, which starts its sweep from $\leq S \; x_v$, passes $x_v$ before the right leaf of pair u passes $x_v$ (FIG. 19). In this case, $I_{tl(p+1)}$ is as defined below.

$I_{tl(p+1)}(x) = \{I_{tlp}(x) \; x < x_v$ $I_{tlp}(x) + \Delta I \; x \geq x_v$ where $\Delta I = I_{urp}(x_v) - I_{tlp}(x_v) = I_3 - I_2$. Once again, $I_{tr(p+1)}(x) = I_{tl(p+1)}(x) - I_t(x)$, where $I_t(x)$ is the target profile to be delivered by the leaf pair t.

In both Type 1 and Type 2 modifications, the other profiles of N(p) are not modified. Since $I_{tr(p+1)}$ differs from $I_{trp}$ for $x \geq x_v$ there is a possibility that N(p+1) has inter-pair separation violations for right leaf positions $x \geq x_v$. Since none of the other right leaf profiles are changed from those of N(p) and since the change in $I_{tl}$ only delays the rightward movement of the left leaf of pair t, no interdigitation violations are possible in N(p+1) for $x < x_v$. It can also be verified that that since $I_{tl0}$ and $I_{tr0}$ are feasible plans that satisfy the maximum velocity constrains, so are $I_{tlp}$ and $I_{trp}$, $p > 0$.

Lemma 8. $I_{jrp}(xStart(j,p))=0$, $1 \leq j \leq m$, $p \geq 0$.

Corollary 6. A Type 2 violation in which $I_{tlp}(x_v)=0$ cannot occur.

Lemma 9. In case of a Type 1 violation, $(I_{tlp}, I_{trp})$ is the same as $(I_{tl0}, I_{tr0})$.

Note that $I_{tlp}(x)$ and $I_{trp}(x)$ are defined only for $x \geq xStart(t,p)$. In the sequel, the convention that $z \geq I_{tlp}(x)(z \geq I_{trp}(x))$ is true is adopted whenever $I_{tlp}(x)(I_{trp}(x))$ is undefined, irrespective of whether z is defined or not.

Lemma 10. Let $F=((I_{1l}, I_{1r}), (I_{2l}, I_{2r}), \ldots, (I_{nl}, I_{nr}))$ be any feasible unidirectional schedule for the desired profile, i.e., a unidirectional schedule that does not violate the interdigitation constraint. Let S(p), be the following assertions.
a. $I_{il}(x) \geq I_{ilp}(x)$, $0 \leq i \leq n$, $x_0 \leq x \leq x_m$
b. $I_{ir}(x) \geq I_{irp}(x)$, $0 \leq i \leq n$, $x_0 \leq x \leq x_m$ S(p) is true for $p \geq 0$.

Lemma 11. For the execution of Algorithm DMLC-INTERDIGITATION
(a) O(n) Type 1 violations can occur.
(b) $O(n^2 m)$ Type 2 violations can occur.
(c) Let $T_{max}$ be the optimal unidirectional therapy time for the input matrix. The time complexity is $O(mn+n*\min\{nm, T_{max}\})$.

Note that Lemma 11 provides two upper bounds of on the complexity of Algorithm DMLC-INTERDIGITATION: $O(n^2 m)$ and $O(n*\max\{m, T_{max}\})$. In most practical situations, $T_{max} < nm$ and so $O(n*\max\{m, T_{max}\})$ can be considered a tighter bound.

Theorem 9. The following are true of the Algorithm DMLC-INTERDIGITATION:
a. The algorithm terminates.
b. The schedule generated is feasible and optimal in therapy time unidirectional schedule.

Example 3

Optimal Leaf Sequencing for Elimination of Tongue-and-Groove Underdosage

The delivery of optimal radiation intensity map produced by the inverse treatment planning system is considered in this Example. The intensity matrix from the optimizer generally has a spatial resolution that is similar to the smallest beamlet size. The beamlet size generally ranges from 5–10 mm. I(x) is the desired intensity profile. The discretized profile from the optimizer gives the intensity values at sample points $x_0, x_1, x_2, \ldots, x_m$. It is assumed that the sample points are uniformly spaced and that $\Delta x = x_{i+1} - x_i$, $0 \leq i < m$. I(x) is assigned the value $I(x_i)$ for $x_i \leq x < x_{i+1}$, for each i. Now, $I(x_i)$ is the desired intensity profile, i.e., $I(x_i)$ is a measure of the number of MUs for which $x_i$, $0 \leq i < m$, needs to be exposed. FIG. 5(b) is referred to again which shows a discretized profile, which is the output from the optimizer. This discretized profile is delivered either with the Segmental Multileaf Collimation (SMLC) method or with Dynamic Multileaf Collimation (DMLC). An SMLC sequence can be transformed to a dynamic leaf sequence by allowing both leaves to start at the same point and close together at the same point, so that they sweep across the same spatial interval. The current Example is developed for SMLC delivery.

In this analysis it is assumed that the beam delivery begins when the pair of leaves is at the left most position. The initial position of the leaves is $x_0$. In this paper, it is assumed that leaves may move only from left to right. That is unidirectional leaf movement is assumed. FIG. 6 is again referred to which illustrates the leaf trajectory during SMLC delivery. Let $I_l(x)$ and $I_r(x_i)$ respectively denote the amount of Monitor Units (Mus) delivered when the left and right leaves leave position $x_i$. Consider the motion of the left leaf. The left leaf begins at $x_0$ and remains here until $I_l(x_0)$ MUs have been delivered. At this time the left leaf is moved to $x_1$, where it remains until $I_l(x_1)$ MUs have been delivered. The left leaf then moves to $x_3$ where it remains until $I_l(x_3)$ MUs have been delivered. At this time, the left leaf is moved to $x_6$, where it remains until $I_l(x_6)$ MUs have been delivered. The final movement of the left leaf is to $x_7$, where it remains until $I_l(x_7) = I_{max}$ MUs have been delivered. At this time the machine is turned off. The total therapy time, $TT(I_l, I_r)$, is the time needed to deliver $I_{max}$ MUs. Note that the term therapy time is used to refer to the beam-on time. The right leaf starts at $x_2$; moves to $x_4$ when $I_r(x_2)$ MUs have been delivered; moves to $x_5$ when $I_r(x_4)$ MUs have been delivered and so on. Note that the machine is off when a leaf is in motion. The following observations are made:
  i. All MUs that are delivered along a radiation beam along $x_i$ before the left leaf passes $x_i$ fall on it. Greater the x value, later the leaf passes that position. Therefore $I_l(x_i)$ is a non-decreasing function.
  ii. All MUs that are delivered along a radiation beam along $x_i$ before the right leaf passes $x_i$, are blocked by the leaf. Greater the x value, later the leaf passes that position.

Therefore $I_r(x_i)$ is also a non-decreasing function.

From these observations, it can be seen that the net amount of MUs delivered at a point is given by $I_l(x_i) - I_r(x_i)$, which must be the same as the desired profile $I(x_i)$.

Once the desired intensity profile, $I(x_i)$ is known, the single leaf pair problem becomes that of determining the individual intensity profiles to be delivered by the left and right leaves, $I_l$ and $I_r$ such that:

$$I(x_i) = I_l(x_i) - I_r(x_i), \ 0 \leq i \leq m \quad (1)$$

$(I_l, I_r)$ is referred to as the treatment plan (or simply plan) for I. Once the plan is obtained, it is possible to determine the movement of both left and right leaves during the therapy. For each i, the left leaf can be allowed to pass $x_i$ when the source has delivered $I_l(x_i)$ MUs. Also, the right leaf can be allowed to pass $x_i$ when the source has delivered $I_r(x_i)$ MUs. A plan is unidirectional if $I_l(x)$ and $I_r(x)$ are unique, $x_0 \leq x \leq x_m$, i.e., each leaf passes over each point only once. The Algorithm SINGLEPAIR is presented below which an be used to obtain a unidirectional plan.

Algorithm SINGLEPAIR
$I_l(x_0) = I(x_0)$
$I_r(x_0) = 0$
For j=1 to m do
  If $(I(x_j) \geq I(x_{j-1}))$
    $I_l(x_j) = I_l(x_{j-1}) + I(x_j) - I(x_{j-1})$
    $I_r(x_j) = I_r(x_{j-1})$
  Else
    $I_r(x_j) = I_r(x_{j-1}) + I(x_{j-1}) - I(x_j)$
    $I_l(x_j) = I_l(x_{j-1})$
End for Theorem 1. Algorithm SINGLEPAIR obtains plans that are optimal in therapy time even when bidirectional leaf movement is permitted.

Corollary 1. Let $I(x_i)$, $0 \leq i \leq m$ be a desired profile. Let $I_l(x_i)$ and $I_r(x_i)$, $0 \leq i \leq m$ be the left and right leaf profiles generated by Algorithm SINGLEPAIR. $I_l(x_i)$ and $I_r(x_i)$, $0 \leq i \leq m$ define optimal therapy time unidirectional left and right leaf profiles for $I(x_i)$, $0 \leq i \leq j$.

Lemma 1. Let $(I_L, I_R)$ be any treatment plan for I. $\Delta(x_i) = I_L(x_i) - I_l(x_i) = I_R(x_i) - I_r(x_i) \geq 0$, $0 \leq i \leq m$.
  (b) $\Delta(x_i)$ is a non-decreasing function.

In a real applications, it is necessary to deliver intensity profiles defined over a 2-D region. Multi-Leaf Collimators (MLCs) are used to deliver such profiles. An MLC is composed of multiple pairs of leaves with parallel axes. FIG. 9 is again referred to which shows an MLC that has three pairs of leaves—(L1,R1), (L2,R2) and (L3,R3) L1,L2,L3 are left leaves and R1,R2,R3 are right leaves. Each pair of leaves is controlled independently. If there are no constraints on the leaf movements, desired profile is divided into a set of parallel profiles defined along the axes of the leaf pairs. Each leaf pair i then delivers the plan for the corresponding intensity profile $I_i(x)$ The set of plans of all leaf pairs forms the solution set, referred to herein as the treatment schedule (or simply schedule). A schedule in which all plans are unidirectional is a unidirectional schedule. Only unidirectional schedules are considered in this Example.

Assume n pairs of leaves. For each pair, there are m sample points. The input is represented as a matrix with n rows and m columns, where the ith row represents the desired intensity profile to be delivered by the ith pair of leaves. The Algorithm SINGLEPAIR is applied to determine the optimal plan for each of the n leaf pairs. This method of generating schedules is described in Algorithm MULTIPAIR shown below. Since the individual plans of the leaf pairs are optimal in therapy time, it can be shown the resulting schedule also is optimum in therapy time.

Algorithm MULTIPAIR
For(i=1; i≤n; i++)
Apply Algorithm SINGLEPAIR to the ith pair of leaves to
  obtain plan $(I_{il}, I_{ir})$ that delivers the intensity profile $I_i(x)$
End For Optimal algorithms with interdigitation and tongue-and-groove constraints are now presented.

In practical situations, there are some constraints regarding movement of the leaves. The minimum separation constraint requires that opposing pairs of leaves be separated by at least some distance $(S_{min})$ at all times during beam delivery. In some MLCs this constraint is applied not only to opposing pairs of leaves, but also to opposing leaves of neighboring pairs. For example, in FIG. 9, L1 and R1, L2 and R2, L3 and R3, L1 and R2, L2 and R1, L2 and R3, L3 and R2 are pairwise subject to the constraint. The term intra-pair minimum separation constraint is used herein to refer to the constraint imposed on an opposing pair of leaves and inter-pair minimum separation constraint to refer to the constraint imposed on opposing leaves of neighboring pairs. The inter-pair minimum separation constraint with $S_{min}=0$ is of special interest and is referred to herein as the interdigitation constraint.

Figure 20:
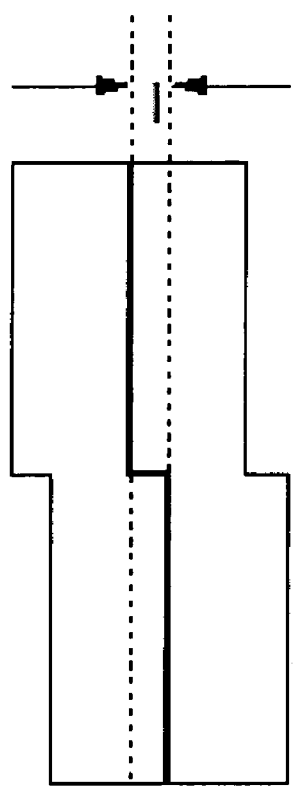
FIG. 20 is a cross section of two adjacent leaves.
Figure 21:
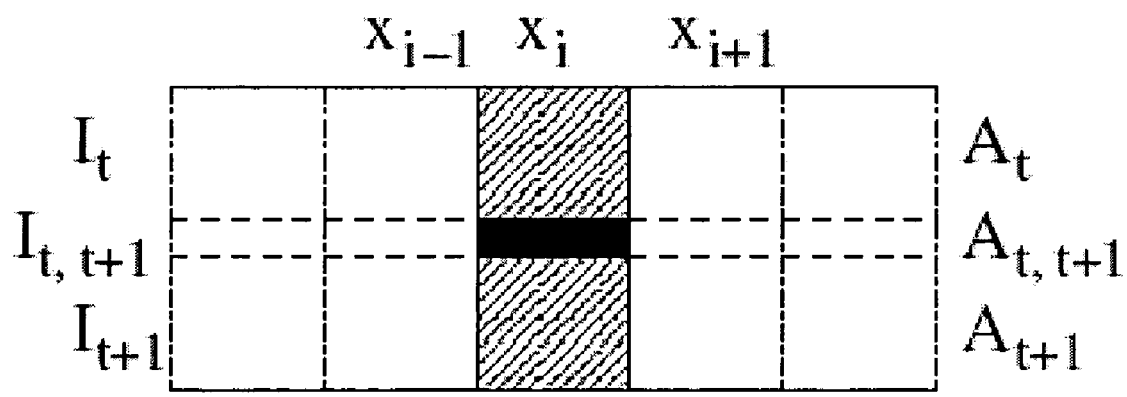
FIG. 21 shows a beams-eye view of the region to be treated by two adjacent leaf pairs.

In most commercially available MLCs, there is a tongue-and-groove arrangement at the interface between adjacent leaves. A cross section of two adjacent leaves is depicted in FIG. 20. The width of the tongue-and-groove region is l. The area under this region gets underdosed due to the mechanical arrangement. FIG. 21 shows a beams-eye view of the region to be treated by two adjacent leaf pairs, t and t+1. Consider the shaded rectangular areas $A_t(x_i)$ and $A_{t+1}(x_i)$ that require exactly $I_t(x_i)$ and $I_{t+1}(x_i)$ MUs to be delivered, respectively. The tongue-and-groove overlap area between the two leaf pairs over the sample point $x_i$, $A_{t,t+1}(x_i)$, is colored black. Let the amount of MUs delivered in $A_{t,t+1}(x_i)$ be $I_{t,t+1}(x_i)$. The following lemma (Lemma 2) is a consequence of the fact that $A_{t,t+1}(x_i)$ is exposed only when both $A_t(x_i)$ and $A_{t+1}(x_i)$ are exposed.

Lemma 2. $I_{t,t+1}(x_i) \leq \min\{I_t(x_i), I_{t+1}(x_i)\}$, $0 \leq i \leq m$, $1 \leq t < n$.

Schedules in which $I_{t,t+1}(x_i) = \min\{I_t(x_i), I_{t+1}(x_i)\}$ are said to be free of tongue-and-groove underdosage effects are now described. Unless treatment schedules are carefully designed, it is possible that $I_{t,t+1}(x_i) << \min\{I_t(x_i), I_{t+1}(x_i)\}$ for some i and t. For example, in a schedule in which $I_{tr}(x_w)=30$, $I_{tl}(x_w)=50$, $I_{(t+1)r}(x_w)=50$ and $I_{(t+1)l}(x_w)=60$, $I_{t,t+1}(x_w) = I_{tl}(x_w) - I_{(t+1)r}(x_w) = 50-50=0$. Note that in this case, $\min\{I_t(x_w), I_{t+1}(x_w)\} = I_{(t+1)l}(x_w) - I_{tl}(x_w) = 60-50=10$. It is clear from this Example that $I_{t,t+1}(x_i)$ could be 0 even when $\min\{I_t(x_i), I_{t+1}(x_i)\}$ is arbitrarily large.

The leaf sequencing algorithms described in Examples 1 (SMLC) and 2 (DMLC) generate schedules that satisfy the inter-pair minimum separation constraint and are optimal in therapy time. However, these algorithms do not account for the tongue-and-groove effect. In this Example, two algorithms are presented. Algorithm TONGUEANDGROOVE generates minimum therapy time unidirectional schedules that are free of tongue-and-groove underdosage. Algorithm TONGUEANDGROOVE-ID generates minimum therapy time unidirectional schedules that are free of tongue-and-groove underdosage while simultaneously satisfying the interdigitation constraint.

The following lemma provides a necessary and sufficient condition for a unidirectional schedule to be free of tongue-and-groove underdosage effects.

Lemma 3. A unidirectional schedule is free of tongue-and-groove underdosage effects if and only if, a. $I_t(x_i)=0$ or $I_{t+1}(x_i)=0$, or b. $I_{tr}(x_i) \leq I_{(t+1)r}(x_i) \leq I_{(t+1)l}(x_i) \leq I_{tl}(x_i)$, or c. $I_{(t+1)r}(x_i) \leq I_{tr}(x_i) \leq I_{tl}(x_i) \leq I_{(t+1)l}(x_i)$, For $0 \leq i \leq m$, $1 \leq t < n$.

Lemma 3 is equivalent to a statement that the time period for which a pair of leaves (say pair t) exposes the region $A_{t,t+1}(x_i)$ is completely contained by the time period for which pair t+1 exposes region $A_{t,t+1}(x_i)$, or vice versa, whenever $I_t(x_i) \neq 0$ and $I_{t+1}(x_i) \neq 0$. Note that if either $I_t(x_i)$ or $I_{t+1}(x_i)$ is zero the containment is not necessary. This necessary and sufficient condition of Lemma 3 is referred to herein as the tongue-and-groove constraint condition. Schedules that satisfy this condition will be said to satisfy the tongue-and-groove constraint.

Note that the schedule generated by Algorithm MULTIPAIR described above may violate the tongue-and-groove constraint. If the schedule has no tongue-and-groove constraint violations, it is the desired optimal schedule. If there are violations in the schedule, all violations of the tongue-and-groove constraint can be theoretically eliminated starting from the left end, i.e., from $x_0$. To eliminate the violations, plans of the schedule that cause the violations are modified. The schedule is scanned from $x_0$ along the positive x direction looking for the least $x_w$ at which there exist leaf pairs u, t, $t \in \{u-1, u+1\}$, that violate the constraint at $x_w$. After rectifying the violation at $x_w$, other violations are checked for. Since the process of eliminating a violation at $x_w$, may at times, lead to new violations at $x_w$, it is sometimes necessary to search afresh from $x_w$ every time a modification is made to the schedule. However, it can be proven that a bound of O(n) on the number of violations that can occur at $x_w$. After eliminating all violations at a particular sample point, $x_w$, the analysis moves to the next point, i.e., increment w and look for possible violations at the new point. The scanning and modification process continues until no tongue-and-groove constraint violations exist. Algorithm TONGUEANDGROOVE shown below outlines the procedure.

Algorithm TONGUEANDGROOVE i. $x=x_0$ ii. While (there is a tongue-and-groove violation) do iii. Find the least $x_w$, $x_w \geq x$, such that there exist leaf pairs u,u+1, that violate the tongue-and-groove constraint at $x_w$.

iv. Modify the schedule to eliminate the violation between leaf pairs u and u+1.

v. $x=x_w$ vi. End While

Let $M=((I_{1l}, I_{1r}), (I_{2l}, I_{2r}), \ldots, (I_{nl}, I_{nr}))$ be the schedule generated by Algorithm MULTIPAIR for the desired intensity profile.

Let $N(p)=((I_{1lp}, I_{1rp}), (I_{2lp}, I_{2rp}), \ldots, (I_{nlp}, I_{nrp}))$ be the schedule obtained after Step (iv) of the Algorithm TONGUEANDGROOVE is applied p times to the input schedule M. Note that M=N(0).

To illustrate the modification process examples are used. To simplify, only two neighboring pairs of leaves are shown. Suppose that the (p+1)th violation occurs between the leaves of pair u and pair t=u+1 at $x_w$. Note that $I_{tlp}(x_w) \neq I_{ulp}(x_w)$, as otherwise, either (b) or (c) of Lemma 3 is true. In case $I_{tlp}(x_w) > I_{ulp}(x_w)$, swap u and t. Now, $I_{tlp}(x_w) < I_{ulp}(x_w)$. In the sequel, these are referred to as u and t values as the u and t of Algorithm TONGUEANDGROOVE. From Lemma 3 and the fact that a violation has occurred, it follows that $I_{trp}(x_w) < I_{urp}(x_w)$. To remove this tongue-and-groove constraint violation, $(I_{tlp}, I_{trp})$ is modified. The other profiles of N(p) are not modified.

The new plan for pair t, $(I_{tl(p+1)}, I_{tr(p+1)})$ is as defined below. If $I_{ulp}(x_w) - I_{tlp}(x_w) \leq I_{urp}(x_w) - I_{trp}(x_w)$, then $$I_{tl(p+1)}(x) = \{I_{tlp}(x) \quad x_0 \leq x < x_w \qquad (2)$$

$$I_{tlp}(x) + \Delta I \quad x_w \leq x \leq x_m$$

where $\Delta I = I_{ulp}(x_w) - I_{tlp}(x_w)$. $I_{tr(p+1)}(x) = I_{tl(p+1)}(x) - I_t(x)$, where $I_t(x)$ is the target profile to be delivered by the leaf pair t.

Otherwise, $$I_{tr(p+1)}(x) = \{I_{trp}(x) \quad x_0 \leq x < x_w \qquad (3)$$

$$I_{trp}(x) + \Delta I' \quad x_w \leq x \leq x_m$$

where ΔI'=$I_{urp}(x_w)-I_{trp}(x_w)$. $I_{tl(p+1)}(x)=I_{tr(p+1)}(x)+I_t(x)$, where $I_t(x)$ is the target profile to be delivered by the leaf pair t.

Figure 22:
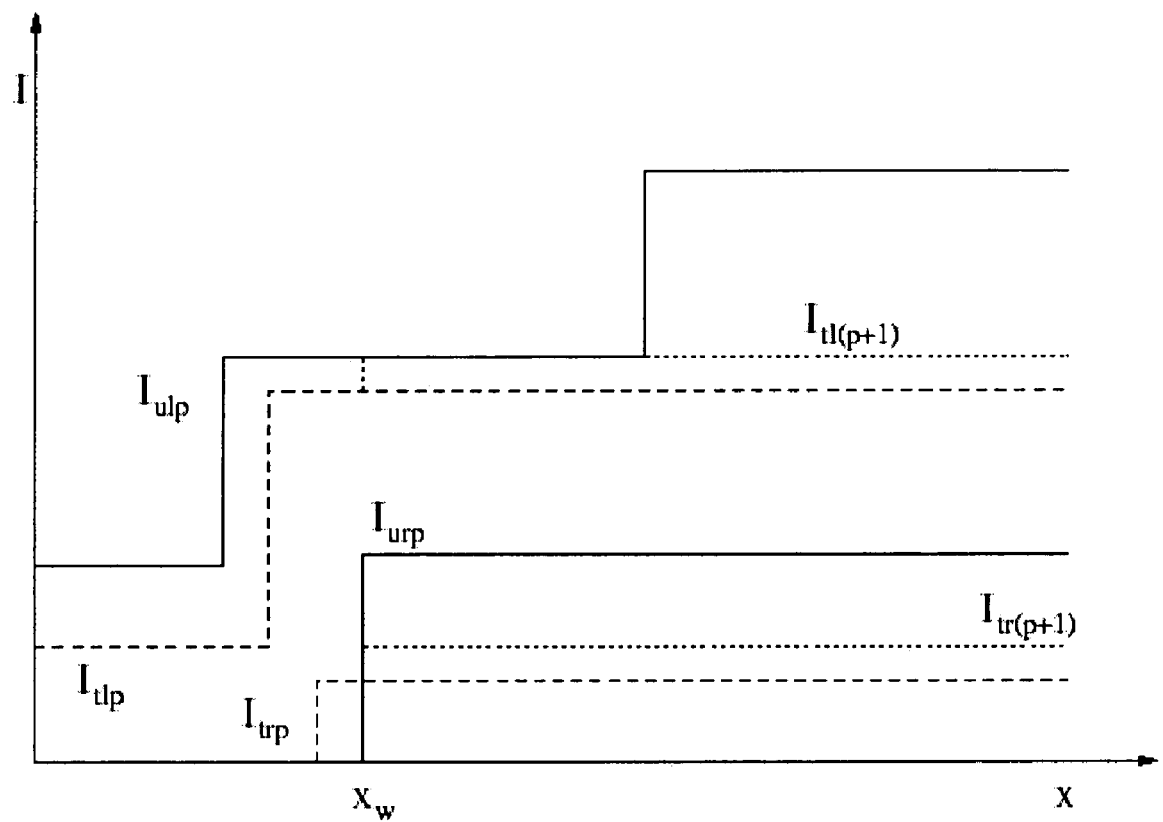
FIG. 22 shows a tongue-and-groove violation.
Figure 23:
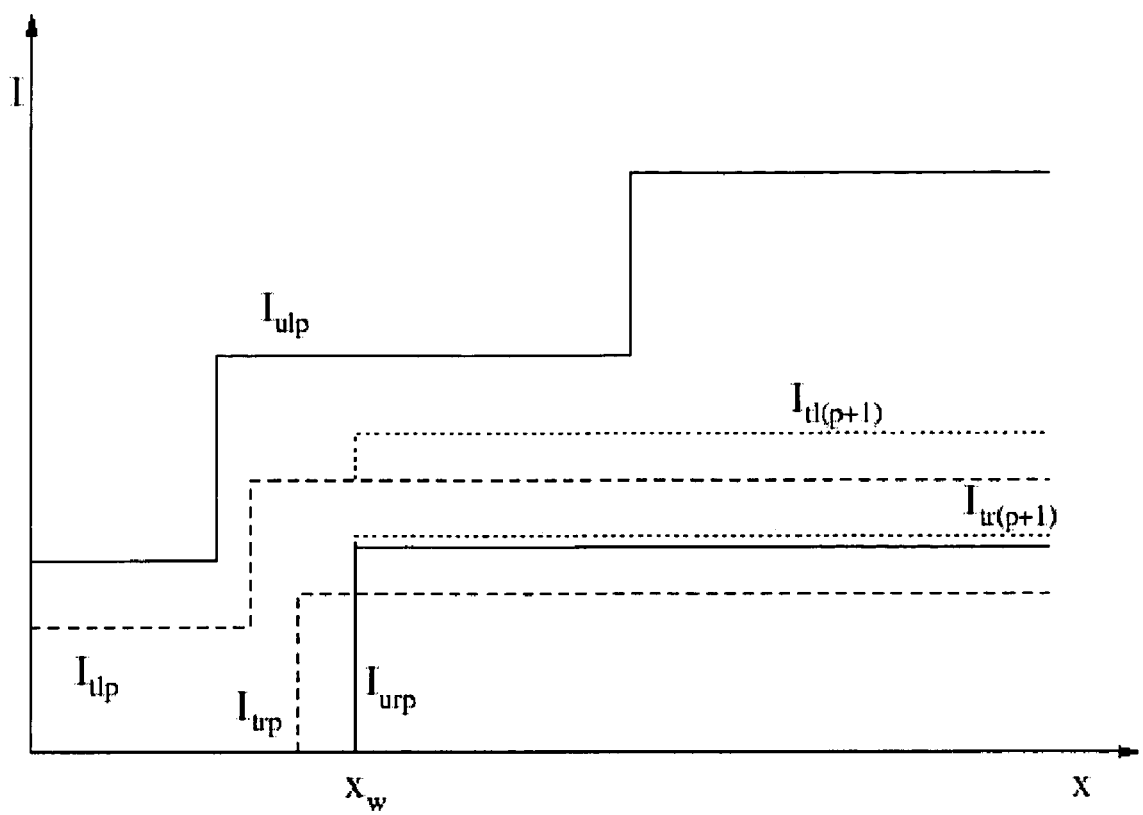
FIG. 23 shows another tongue-and-groove violation.

The former case is illustrated in FIG. 22 and the latter case is illustrated in FIG. 23.

Since $(I_{tl(p+1)},I_{tr(p+1)})$ differs from $(I_{tlp},I_{trp})$ for $x \geq x_w$ there is a possibility that N(p+1) is involved in tongue-and-groove violations for $x \geq x_w$. Since none of the other leaf profiles are changed from those of N(p) no tongue-and-groove constraint violations are possible in N(p+1) for $x < x_w$. One may also verify that since $I_{tl0}$ and $I_{tr0}$ are non-decreasing functions of x, so also are $I_{tlp}$ and $I_{trp}$, p>0.

Lemma 4. Let F=(($I_{1l},I_{1r}$),($I_{2l},I_{2r}$), . . . ,($I_{nl},I_{nr}$)) be any unidirectional schedule for the desired profile that satisfies the tongue-and-groove constraint. Let S(p), be the following assertions.

a. $I_{il}(x) \geq I_{ilp}(x)$, $0 \leq i \leq n$, $x_0 \leq x \leq x_m$
b. $I_{ir}(x) \geq I_{irp}(x)$, $0 \leq i \leq n$, $x_0 \leq x \leq x_m$ S(p) is true for $p \geq 0$.

Algorithms for the elimination of tongue-and-groove effect and interdigitation will now be described. As pointed out above, the elimination of tongue-and-groove constraint violations does not guarantee elimination of interdigitation constraint violations. Therefore the schedule generated by Algorithm TONGUEANDGROOVE may not be free of interdigitation violations. The algorithm described herein for obtaining schedules that simultaneously satisfy both constraints, Algorithm TONGUEANDGROOVE-ID, is similar to Algorithm TONGUEANDGROOVE. The only difference between the two algorithms lies in the definition of the constraint condition. To be precise, the following definition is provided:

Definition 1. A unidirectional schedule is said to satisfy the tongue-and-groove-id constraint if
i. $I_{tr}(x_i) \leq I_{(t+1)r}(x_i) \leq I_{t+1)l}(x_i) \leq I_{tl}(x_i)$, or
ii. $I_{(t+1)r}(x_i) \leq I_{tr}(x_i) \leq I_{tl}(x_i) \leq I_{(t+1)l}(x_i)$, For $0 \leq i \leq m$, $1 \leq t < n$.

The only difference between this constraint and the tongue-and-groove constraint is that this constraint enforces condition (a) or (b) above to be true at all sample points $x_i$ including those at which $I_t(x_i)=0$ and/or $I_{t+1}(x_i)=0$.

Lemma 5. A schedule satisfies the tongue-and-groove-id constraint if it satisfies the tongue-and-groove constraint and the interdigitation constraint.

Algorithm TONGUEANDGROOVE-ID finds violations of the tongue-and-groove-id constraint from left to right in exactly the same manner in which Algorithm TONGUEANDGROOVE detects tongue-and-groove violations. Also, the violations are eliminated as before, i.e., as prescribed by Equations 2 and 3 and illustrated in FIGS. 22 and 23, respectively. Algorithm TONGUEANDGROOVE-ID is shown below. All notation used in the algorithm and the related discussion in the remainder of this example is also the same as that used above and corresponds directly to the usage in Algorithm TONGUEANDGROOVE.

Algorithm TONGUEANDGROOVE-ID
i. $x=x_0$
ii. While (there is a tongue-and-groove-id violation) do
iii. Find the least $x_w$, $x_w \geq x$, such that there exist leaf pairs u,u+1, that violate the tongue-and-groove-id constraint at $x_w$.
iv. Modify the schedule to eliminate the violation between leaf pairs u and u+1.
v. $x=x_w$
vi. End While In the remainder of this example the term "algorithm" is used to refer to the Algorithm TONGUEANDGROOVE or Algorithm TONGUEANDGROOVE-ID and "violation" is used to refer to tongue-and-groove constraint violation or tongue-and-groove-id constraint violation (depending on which algorithm is considered), unless explicitly mentioned.

The execution of the algorithm starts with schedule M at $x=x_0$ and sweeps to the right, eliminating violations from the schedule along the way. The modifications applied to eliminate a violation at $x_w$, prescribed by Equations 2 and 3, modify one of the violating profiles for $x \geq x_w$. From the unidirectional nature of the sweep of the algorithm, it is clear that the modification of the profile for $x > x_w$ can have no consequence on violations that may occur at the point $x_w$. Therefore it suffices to modify the profile only at $x_w$ at the time the violation at $x_w$ is detected. The modification can be propagated to the right as the algorithm sweeps. This can be done by using an (n×m) matrix A that keeps track of the amount by which the profiles have been raised. A(j,k) denotes the cumulative amount by which the jth leaf pair profiles have been raised at sample point $x_k$ from the schedule M generated using Algorithm MULTIPAIR. When the algorithm has eliminated all violations at each $x_w$, it moves to $x_{w+1}$ to look for possible violations. It first sets the (w+1)th column of the modification matrix equal to the wth column to reflect rightward propagation of the modifications. It then looks for and eliminates violations at $x_{w+1}$ and so on.

The process of detecting the violations at $x_w$ is described further. It is shown below that if one carefully selects the order in which violations are detected and eliminated, the number of violations at each $x_w$, $0 \leq w \leq m$ will be O(n).

Lemma 6. The algorithm can be implemented such that O(n) violations occur at each $x_w$, $0 \leq w \leq m$.

The bound is achieved using a two pass scheme at $x_w$. In pass one adjacent leaf pairs (1,2),(2,3), . . . ,(n−1,n) are checked, in that order, for possible violations at $x_w$. In pass two, violations are checked for in the reverse order, i.e., (n−1,n),(n−2,n−1), . . . ,(1,2). So each set of adjacent pairs (i,i+1), $1 \leq i < n$ is checked exactly twice for possible violations. It can be seen that if a violation is detected in pass one, either the profile of leaf pair i or that of leaf pair i+1 may be modified (raised) to eliminate the violation. However, in pass two only the profile of pair i may be modified. This is because the profile of pair i is not modified between the two times it is checked for violations with pair i+1. The profile of pair i+1, on the other hand, could have been modified between these times as a result of violations with pair i+2. Therefore in pass two, only i can be a candidate for t (where t is as explained in the algorithm) when pairs (i,i+1) are examined. From this it also follows that when pairs (i−1,i) are subsequently examined in pass two, the profile of pair i will not be modified. Since there is no violation between adjacent pairs (1,2),(2,3), . . . , (i,i+1) at that time and none of these pairs is ever examined again, it follows that at the end of pass two there can be no violations between pairs (i,i+1), $1 \leq i < n$.

Lemma 7. For the execution of the algorithm, the time complexity is O(nm) Follows from Lemma 6 and the fact that there are m sample points.

Theorem 2.
a. Algorithms TONGUEANDGROOOVE and TONGUEANDGROOVE-ID terminate.
b. The schedule generated by Algorithm TONGUEANDGROOVE is free of tongue-and-groove constraint violations and is optimal in therapy time for unidirectional schedules.

c. The schedule generated by Algorithm TONGUEANDGROOVE-ID is free of interdigitation and tongue-and-groove constraint violations and is optimal in therapy time for unidirectional schedules.

It is to be understood that while the invention has been described in conjunction with the preferred specific embodiments thereof, that the foregoing description as well as the examples which follow are intended to illustrate and not limit the scope of the invention. Other aspects, advantages and modifications within the scope of the invention will be apparent to those skilled in the art to which the invention pertains.

We claim:

1. A method of delivering radiation treatment using multi-leaf collimation, comprising the steps of:
   (a) providing a radiation fluence map which supplies a desired intensity profile;
   (b) converting said fluence map into a preliminary leaf sequence, wherein said preliminary leaf sequence minimizes machine on-time and is generated without any leaf movement constraints;
   (c) imposing at least one leaf movement constraint on said preliminary leaf sequence, and
   (d) applying at least one constraint elimination algorithm, said algorithm adjusting said preliminary leaf sequence to minimize violations of said constraint while providing said fluence map and said minimized on-time.

2. The method of claim 1, wherein said multi-leaf collimation is segmented multi-leaf collimation.

3. The method of claim 2, wherein said constraint comprises a minimum separation distance between adjacent leaves in said leaf pair, said applying step (d) comprising:
   (e) modifying at least one leaf pair in said preliminary leaf sequence to form a modified leaf sequence, wherein said modifying step comprises identifying and adjusting positions of leaves in said preliminary leaf sequence which violate said minimum separation distance to provide at least said minimum separation distance;
   (f) modifying at least one leaf pair in said modified leaf sequence to produce a further modified leaf sequence, said further modified leaf sequence providing said intensity profile;
   (g) examining said further modified leaf sequence for violations of said minimum separation distance, and
   (h) iteratively repeating said steps (e) and (f) if at least one violation of said minimum separation distance is identified in step (g) using said further modified leaf sequence as said preliminary leaf sequence to generate a corrected leaf sequence.

4. The method of claim 3, further comprising the step of reducing a tongue-and-groove underdose, said step of reducing said tongue-and-groove underdose comprising applying a tongue-and-groove constraint to said corrected leaf sequence, said applying a tongue-and-groove constraint step comprising the steps of:
   (i) modifying at least one leaf pair in said corrected leaf sequence to form a modified corrected leaf sequence, wherein said modifying step comprises identifying and adjusting positions of leaves in said preliminary leaf sequence which violate a tongue-and-groove constraint;
   (j) modifying at least one leaf pair in said modified corrected leaf sequence to produce a further modified leaf sequence, said further modified leaf sequence providing said fluence map;
   (k) examining said further modified corrected leaf sequence for violations of tongue-and-groove constraint, and
   (l) iteratively repeating said steps (i) and (j) if at least one violation of said tongue and groove constraint is identified in step (k) using said further modified leaf sequence as said preliminary leaf sequence.

5. The method of claim 1, wherein said multi-leaf collimation is dynamic multi-leaf collimation.

6. The method of claim 5, wherein said constraint comprises a leaf interdigitation constraint, said applying step (d) comprises:
   (e) modifying at least one leaf pair in said preliminary leaf sequence to form a modified leaf sequence, wherein said modifying step comprises identifying and adjusting positions of leaves in said preliminary leaf sequence which violate said interdigitation constraint;
   (f) modifying at least one leaf pair in said modified leaf sequence to produce a further modified leaf sequence, said further modified leaf sequence providing said fluence map;
   (g) examining said further modified leaf sequence for violations of said interdigitation constraint, and
   (h) iteratively repeating said steps (e) and (f) if at least one violation of said interdigitation constraint is identified in step (g) using said further modified leaf sequence as said preliminary leaf sequence.

7. A method of reducing tongue-and-groove underdose during radiation treatment using multi-leaf collimation, comprising the steps of:
   (a) providing a radiation fluence map which supplies a desired intensity profile;
   (b) converting said fluence map into a preliminary leaf sequence, wherein said preliminary leaf sequence minimizes a minimum on-time and is generated without any leaf movement constraints;
   (c) modifying at least one leaf pair in said preliminary leaf sequence to form a modified leaf sequence, wherein said modifying step comprises identifying and adjusting positions of leaves in said preliminary leaf sequence which violate a tongue-and-groove constraint;
   (d) modifying at least one leaf pair in said modified leaf sequence to produce a further modified leaf sequence, said further modified leaf sequence providing said intensity profile;
   (e) examining said further modified leaf sequence for violations of said tongue-and-groove constraint, and
   (f) iteratively repeating said steps (c) and (d) if at least one violation of said tongue-and-groove constraint is identified in step (e) using said further modified leaf sequence as said preliminary leaf sequence.

8. A system for delivering radiation treatment using multi-leaf collimation, comprising:
   a radiation source for generating a radiation beam;
   a multi-leaf collimator having a plurality of leafs for shaping said radiation beam;
   structure for generating a preliminary leaf sequence from a fluence map, wherein said preliminary leaf sequence minimizes machine on-time and is generated without any leaf movement constraints;
   structure for imposing at least one leaf movement constraint on said preliminary leaf sequence, and
   structure for applying at least one constraint elimination algorithm, said algorithm adjusting said preliminary leaf sequence to minimize violations of said constraint while providing said fluence map and said minimized on-time.

9. The system of claim 8, wherein said multi-leaf collimator is a segmented multi-leaf collimator.

10. The system of claim 8, wherein said multi-leaf collimator is a dynamic multi-leaf collimator.

11. The system of claim 8, further comprising structure for reducing a tongue-and-groove underdose.

12. The system of claim 8, wherein said constraint comprises a minimum separation distance between paired ones of said leaves, said structure for applying comprises:

structure for modifying at least one leaf pair in said preliminary leaf sequence to form a modified leaf sequence, wherein said structure for modifying comprises structure for identifying and adjusting positions of leaves in said preliminary leaf sequence which violate said minimum separation distance to provide at least said minimum separation distance;

structure for modifying at least one leaf pair in said modified leaf sequence to produce a further modified leaf sequence, said further modified leaf sequence providing said intensity profile;

structure for examining said further modified leaf sequence for violations of said minimum separation distance, and structure for iteratively adjusting said leaf sequence if at least one violation of said minimum separation distance is identified.

* * * * *